US010682105B2

(12) United States Patent
Shimizukawa et al.

(10) Patent No.: US 10,682,105 B2
(45) Date of Patent: Jun. 16, 2020

(54) ELECTRONIC CASSETTE AND OPERATING METHOD THEREOF

(71) Applicant: FUJIFILM Corporation, Tokyo (JP)

(72) Inventors: Sho Shimizukawa, Ashigarakami-gun (JP); Makoto Kitada, Ashigarakami-gun (JP); Jun Enomoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 86 days.

(21) Appl. No.: 16/058,657

(22) Filed: Aug. 8, 2018

(65) Prior Publication Data

US 2018/0368789 A1 Dec. 27, 2018

Related U.S. Application Data

(63) Continuation of application No. 14/867,859, filed on Sep. 28, 2015, now Pat. No. 10,105,114.

(30) Foreign Application Priority Data

Sep. 29, 2014 (JP) ................. 2014-199345

(51) Int. Cl.
*A61B 6/00* (2006.01)
(52) U.S. Cl.
CPC .............. *A61B 6/4283* (2013.01); *A61B 6/42* (2013.01); *A61B 6/4208* (2013.01);
(Continued)

(58) Field of Classification Search
CPC ....... A61B 6/42; A61B 6/4208; A61B 6/4233; A61B 6/4283; A61B 6/44; A61B 6/4405;
(Continued)

(56) References Cited

U.S. PATENT DOCUMENTS 5,877,501 A 3/1999 Ivan et al.
7,250,608 B2 * 7/2007 Ozeki ................... G01T 1/2018
250/370.01
(Continued)

FOREIGN PATENT DOCUMENTS

JP 2005-3755 A 1/2005
JP 2011-232667 A 11/2011
(Continued)

OTHER PUBLICATIONS

Japanese Office Action and English translation, dated Jun. 7, 2017, for corresponding Japanese Application No. 2014-199345.
(Continued)

*Primary Examiner* — Allen C. Ho
(74) *Attorney, Agent, or Firm* — Birch, Stewart, Kolasch & Birch, LLP

(57) ABSTRACT

An electronic cassette comprises a main battery which is detachably attached to a battery loading unit, and a sub-battery which supplies electricity to a bias power circuit and so on in substitution for the main battery. A power source selector changes the power source to the sub-battery from the main battery when it is judged that a replacement operation of the main battery is started. Since supply of the electricity to the bias power circuit is continued, and the bias voltage continues being applied to a photoelectric converter without a break, there is no need to perform a photoelectric conversion stabilizing process and an offset correction image detecting process after turning on of the main power. Therefore, a start-up time TR2 is largely shortened from a start-up time TR1.

15 Claims, 15 Drawing Sheets

(52) U.S. Cl.
CPC .............. *A61B 6/4233* (2013.01); *A61B 6/44* (2013.01); *A61B 6/4405* (2013.01); *A61B 6/4411* (2013.01); *A61B 6/4452* (2013.01); *A61B 6/54* (2013.01); *A61B 6/56* (2013.01)

(58) Field of Classification Search
CPC ....... A61B 6/4411; A61B 6/4452; A61B 6/54; A61B 6/56
USPC ...... 378/98.8, 189, 91, 114–116; 250/370.09
See application file for complete search history.

(56) References Cited

U.S. PATENT DOCUMENTS

| | | | |
|---|---|---|---|
| 7,365,337 B2* | 4/2008 | Tsuchino | A61B 6/56 250/370.09 |
| 7,462,834 B2* | 12/2008 | Masazumi | G01T 1/24 250/370.09 |
| 7,482,595 B1 | 1/2009 | Ertel | |
| 7,545,914 B2 | 6/2009 | Kito et al. | |
| 7,561,668 B2 | 7/2009 | Ohta et al. | |
| 7,593,507 B2* | 9/2009 | Ohta | A61B 6/032 378/207 |
| 7,712,959 B2 | 5/2010 | Tanabe et al. | |
| 7,732,779 B2* | 6/2010 | Kito | A61B 6/548 250/370.09 |
| 7,740,405 B2 | 6/2010 | Ohta et al. | |
| 7,751,529 B2* | 7/2010 | Ohara | A61B 6/00 378/116 |
| 7,777,193 B2* | 8/2010 | Kito | G01T 7/00 250/370.09 |
| 7,807,976 B2* | 10/2010 | Ohta | A61B 6/4233 250/370.09 |
| 7,991,119 B2* | 8/2011 | Yoshida | G01T 1/00 378/114 |
| 8,080,802 B2* | 12/2011 | Nishino | A61B 6/4233 250/370.08 |
| 8,183,822 B2* | 5/2012 | Tsubota | H02J 7/00036 320/106 |
| 8,193,509 B2* | 6/2012 | Niekawa | A61B 6/4233 250/370.09 |
| 8,198,593 B2 | 6/2012 | Kito et al. | |
| 8,334,516 B2* | 12/2012 | Tsubota | A61B 6/4283 250/370.08 |
| 8,362,437 B2 | 1/2013 | Tsubota et al. | |
| 8,399,846 B2* | 3/2013 | Niekawa | A61B 6/4233 250/370.08 |
| 8,461,544 B2 | 6/2013 | Iwakiri et al. | |
| 8,532,262 B2* | 9/2013 | Iwakiri | A61B 6/4233 250/370.09 |
| 8,536,535 B2 | 9/2013 | Amitani et al. | |
| 8,546,777 B2 | 10/2013 | Utsunomiya | |
| 8,550,709 B2* | 10/2013 | Nishino | A61B 6/04 378/145 |
| 8,576,087 B2* | 11/2013 | Kamiya | A61B 6/4283 250/318 |
| 8,586,934 B2* | 11/2013 | Nakatsugawa | G01T 1/2985 250/363.02 |
| 8,664,615 B2* | 3/2014 | Amitani | A61B 6/00 250/370.09 |
| 8,705,700 B2* | 4/2014 | Eguchi | A61B 6/4233 378/116 |
| 8,731,141 B2* | 5/2014 | Kuwabara | A61B 6/00 378/116 |
| 8,748,839 B2 | 6/2014 | Tajima | |
| 8,750,455 B2 | 6/2014 | Kondou | |
| 8,767,919 B2* | 7/2014 | Nishino | A61B 6/4007 378/108 |
| 8,785,871 B2* | 7/2014 | Muraoka | A61B 6/4233 250/370.09 |
| 8,785,876 B2* | 7/2014 | Tajima | A61B 6/4233 250/363.02 |
| 8,786,257 B2* | 7/2014 | Eguchi | A61B 6/00 320/127 |
| 8,787,528 B2 | 7/2014 | Kamiya et al. | |
| 8,798,235 B2* | 8/2014 | Ohta | A61B 6/4494 378/102 |
| 8,798,236 B2* | 8/2014 | Ohta | A61B 6/4494 250/370.09 |
| 8,835,862 B2* | 9/2014 | Tajima | H04N 5/32 250/370.09 |
| 8,847,167 B2 | 9/2014 | Tajima | |
| 8,861,678 B2* | 10/2014 | Liu | H05G 1/08 378/91 |
| 8,866,095 B2* | 10/2014 | Oguma | A61B 6/4233 250/370.09 |
| 8,867,702 B2* | 10/2014 | Nishino | A61B 6/4007 378/63 |
| 8,885,909 B2* | 11/2014 | Takagi | G06T 5/20 382/132 |
| 8,891,733 B2* | 11/2014 | Liu | A61B 6/4405 378/91 |
| 8,929,510 B2* | 1/2015 | Nishino | A61B 6/4216 378/102 |
| 8,942,350 B2 | 1/2015 | Iwase | |
| 9,024,244 B2* | 5/2015 | Amitani | H01L 27/14618 250/208.1 |
| 9,035,263 B2 | 5/2015 | Iwata et al. | |
| 9,044,191 B2* | 6/2015 | Nishino | A61B 6/4405 |
| 9,050,059 B2* | 6/2015 | Kuwabara | A61B 6/542 |
| 9,063,236 B2 | 6/2015 | Shikino | |
| 9,078,624 B2* | 7/2015 | Sugizaki | G01T 1/2928 |
| 9,128,368 B2* | 9/2015 | Tajima | G03B 42/02 |
| 9,168,016 B2* | 10/2015 | Ohta | G01T 1/24 |
| 9,186,118 B2* | 11/2015 | Yonekawa | A61B 6/4233 |
| 9,216,006 B2* | 12/2015 | Kuwabara | A61B 6/4233 |
| 9,232,620 B2 | 1/2016 | Tajima | |
| 9,258,464 B2 | 2/2016 | Ohta et al. | |
| 9,258,497 B2 | 2/2016 | Tsuji | |
| 9,259,201 B2* | 2/2016 | Sato | A61B 6/4233 |
| 9,265,476 B2 | 2/2016 | Iwakiri et al. | |
| 9,301,725 B2 | 4/2016 | Kaneko et al. | |
| 9,320,483 B2* | 4/2016 | Kobayashi | A61B 6/00 |
| 9,322,934 B2* | 4/2016 | Ogura | G01T 1/2006 |
| 9,380,988 B2* | 7/2016 | Kitano | A61B 6/4283 |
| 9,405,183 B2* | 8/2016 | Ando | A61B 6/4266 |
| 9,414,802 B2 | 8/2016 | Urbon et al. | |
| 9,521,983 B2 | 12/2016 | Jang et al. | |
| 9,521,986 B2 | 12/2016 | Ozawa et al. | |
| 9,535,176 B2 | 1/2017 | Miyoshi et al. | |
| 9,569,829 B2* | 2/2017 | Ohguri | H04N 5/2254 |
| 9,661,728 B2* | 5/2017 | Eguchi | H05G 1/08 |
| 9,662,086 B2* | 5/2017 | Ohta | A61B 5/0059 |
| 9,668,331 B2* | 5/2017 | Takahashi | H04N 5/32 |
| 9,668,706 B2* | 6/2017 | Kim | A61B 6/547 |
| 9,675,314 B2 | 6/2017 | Ota et al. | |
| 9,700,271 B2* | 7/2017 | Horiuchi | A61B 6/4405 |
| 9,750,477 B2* | 9/2017 | Kitagawa | A61B 6/542 |
| 9,778,380 B2* | 10/2017 | Enomoto | G01T 1/161 |
| 9,788,809 B2* | 10/2017 | Hiroike | A61B 6/4233 |
| 9,826,946 B2* | 11/2017 | Ota | A61B 6/4233 |
| 9,880,111 B2* | 1/2018 | Oda | H04N 5/32 |
| 9,955,931 B2* | 5/2018 | Bettouyashiki | A61B 6/4283 |
| 9,968,315 B2* | 5/2018 | Ogura | A61B 6/4283 |
| 10,022,102 B2* | 7/2018 | Okada | A61B 6/542 |
| 10,058,297 B2* | 8/2018 | Park | A61B 6/4494 |
| 10,105,114 B2* | 10/2018 | Shimizukawa | A61B 6/4283 |
| 10,327,729 B2* | 6/2019 | Hayashi | A61B 6/566 |
| 10,335,111 B2* | 7/2019 | Enomoto | A61B 6/56 |
| 10,342,508 B2* | 7/2019 | Matsushita | A61B 6/548 |
| 10,368,826 B2* | 8/2019 | Tamura | A61B 6/4266 |
| 10,416,320 B2* | 9/2019 | Kondo | G01T 1/2023 |

FOREIGN PATENT DOCUMENTS

| | | | | |
|---|---|---|---|---|
| JP | 2014-142355 A | * | 8/2014 | ............ A61B 6/00 |
| JP | 2014-142355 A | | 8/2014 | |
| JP | 2014-160046 A | | 9/2014 | |

(56) References Cited

OTHER PUBLICATIONS

U.S. Office Action issued in corresponding U.S. Appl. No. 14/867,859 dated Feb. 14, 2018.
U.S. Office Action issued in corresponding U.S. Appl. No. 14/867,859 dated Jun. 29, 2017.

* cited by examiner

ELECTRONIC CASSETTE AND OPERATING METHOD THEREOF

CROSS-REFERENCE TO RELATED APPLICATIONS

The present application is a continuation of copending application Ser. No. 14/867,859, filed on Sep. 28, 2015, now U.S. Pat. No. 10,105,114 B2 issued on Oct. 23, 2018, which claims priority under 35 U.S.C. § 119(a) to Japanese Patent Application No. 2014-199345, filed in JAPAN on Sept. 29, 2014. The above applications are hereby expressly incorporated by reference, in their entirety, into the present application.

BACKGROUND OF THE INVENTION

1. Field of the Invention

The present invention relates to an electronic cassette used for radiography and an operation method of an electronic cassette.

2. Description Related to the Prior Art

In medical radiography, e.g., radiography, an electronic cassette is used widely. The electronic cassette has a constitution that an image detection unit (it is also called a flat panel detector (FPD)) which detects an X-ray image of a subject such as a patient is accommodated within a housing of portable type.

For example, the image detection unit is composed of a scintillator which converts X-rays into visible light and emits it and a photo detection substrate which detects the emitted visible light from the scintillator and converts it into an electric signal.

The photo detection substrate includes a plurality of pixels arranged two-dimensionally. The pixel is composed of a photoelectric converter which responds to visible light and produces and accumulates electric charge, and a switching element such as a TFT (Thin Film Transistor) which is connected to the photoelectric converter for reading the electric charge accumulated in the photoelectric converter. A bias voltage is applied to the photoelectric converter from a bias power circuit.

As stated in Japanese Patent Laid-Open Publication No. 2014-160046, there is an electronic cassette usable without a cable, by comprising a radio communication unit performing radio communication with an external equipment such as a control unit controlling operations of the electronic cassette and a battery to supply electricity to drive the electronic cassette. In Japanese Patent Laid-Open Publication No. 2014-160046, the battery supplies electricity to sections of the electronic cassette such as a bias power circuit.

As stated in Japanese Patent Laid-Open Publication No. 2014-142355, a battery is detachably attached in a housing. When remaining capacity of the battery has reduced, an operator such as a radiology technician removes the battery from the housing and replaces with another battery which has been charged.

In addition, Japanese Patent Laid-Open Publication No. 2014-160046 states that an offset correction is performed to remove influence of a fixed pattern noise due to operating environment of the electronic cassette from an X-ray image. As is generally known, the offset correction is a process that the image detection unit detects an image (image for offset correction) in the state that X-rays are not irradiated, and the image for offset correction is deducted pixel-by-pixel basis from an X-ray image which the image detection unit detected based on X-rays which transmitted through an object.

When the battery is detached from the housing for exchange, since electricity is not supplied to the bias power circuit and other sections, a bias voltage is not applied to the photoelectric converter. Therefore, it takes a long start-up time from turning on of the main power of the electronic cassette after the exchange of the battery to a state that photographing preparation is completed to perform X-rays photography. The reason is that a detection of an image for offset correction should be performed again when an application of bias voltage is stopped once and then re-started, and it takes a long time for stabilization of the operation of the photoelectric converter which is necessary to detect the image for offset correction precisely.

So far, when a battery is exchanged in the middle of radiography, re-start of the radiography is delayed due to the long start-up time, and a stress to an object and a reduction in photography efficiency are caused. Therefore, it has been demanded shortening of the start-up time when a battery is exchanged.

SUMMARY OF THE INVENTION

An object of the present invention is to provide an electronic cassette which can shorten a start-up time when a battery is exchanged, and an operation method of the electronic cassette.

To achieve the above and other objects, an electronic cassette of the present invention comprises an image detection unit, a housing of portable type, a photoelectric converter, a bias power circuit, a main battery, a sub-battery and a power source selector. The image detection unit has a pixel to detect a radiation image of an object based on radiation that penetrated the object. The housing of portable type contains the image detection unit. The photoelectric converter constitutes the pixel, generates electric charge in response to visible light converted from the radiation, and accumulates the electric charge. The bias power circuit applies bias voltage to the photoelectric converter. The main battery is detachably attached to the housing and supplies electricity to the bias power circuit. The sub-battery supplies electricity to the bias power circuit in substitution for the main battery. The power source selector judges whether a replacement operation of the main battery is started, and changes the power source for the bias power circuit from the main battery to the sub-battery when the power source selector judges that the replacement operation is started.

It is preferable that the electronic cassette further comprises a detachment detection unit which detects whether a detachment operation of the main battery from the housing is started, and the power source selector judges that the replacement operation is started and changes the power source of the bias power circuit to the sub-battery when the detachment detection unit detects a start of the detachment operation.

It is preferable that the electronic cassette further comprises a main power switch for operating on/off of a main power of the electronic cassette and a first timer which times a first elapsed time after the main power switch is turned off, and the power source selector continues to supply of the electricity from the main battery till the first elapsed time reaches a predetermined first set time after the main power switch is turned off, and stops the supply of the electricity from the main battery after the first elapsed time reaches the first set time even when the detachment detection unit does not detect the start of the detachment operation.

It is also preferable that the electronic cassette further comprises a main power switch for operating on/off of a main power of the electronic cassette, and the power source selector judges that the replacement operation is started when the main power switch is turned off.

It is preferable that the electronic cassette further comprises a second timer which times a second elapsed time after the power source selector changes the power source to the sub-battery, and the power source selector continues to supply of the electricity from the sub-battery till the second elapsed time reaches a predetermined second set time, and stops the supply of the electricity from the sub-battery after the second elapsed time reaches the second set time.

It is preferable that the power source selector changes the power source for the bias power circuit to the main battery when the main power is turned on while the sub-battery supplies electricity.

It is preferable that the pixel is constituted of the photoelectric converter and a switching element connected to the photoelectric converter to read electric charge, the electronic cassette further comprises a driving circuit which drives the switching element and a first power supply circuit which supplies a drive voltage for the switching element to the driving circuit, and electricity is supplied to the first power supply circuit from the sub-battery.

It is preferable that the electronic cassette further comprises a signal processor which converts electric charge into an image signal constituting the radiation image and a second power supply circuit which supplies a drive voltage to the signal processor, and electricity is supplied to the second power supply circuit from the sub-battery.

It is preferable that the electronic cassette further comprises an impact history acquiring unit including an impact detection sensor which detects an impact to the housing, a storage section which stores an output from the impact detection sensor, and a storage control section which controls recording of the output from the impact detection sensor to the storage section, and a third power supply circuit which supplies a drive voltage to the impact history acquiring unit, and electricity is supplied to the third power supply circuit from the sub-battery.

It is preferable that the electronic cassette further comprises a charging circuit which charges the sub-battery with electricity from the main battery.

In an operating method of an electronic cassette of the present invention, the electronic cassette comprises an image detection unit, a housing of portable type, a photoelectric converter, a bias power circuit, a main battery and a sub-battery. The image detection unit has a pixel to detect a radiation image of an object based on radiation that penetrated the object. The housing of portable type contains the image detection unit. The photoelectric converter constitutes the pixel, generates electric charge in response to visible light converted from the radiation, and accumulates the electric charge. The bias power circuit applies bias voltage to the photoelectric converter. The main battery is detachably attached to the housing and supplies electricity to the bias power circuit. The sub-battery supplies electricity to the bias power circuit in substitution for the main battery. The operating method of the electronic cassette comprises steps of judging whether a replacement operation of the main battery is started, and changing the power source for the bias power circuit from the main battery to the sub-battery when it is judged in the judging step that the replacement operation is started.

According to the present invention, since a sub-battery which supplies electricity to the bias power circuit in substitution for the main battery is provided in addition to a main battery which is detachably attached to the housing and supplies electricity to the bias power circuit, and the power source is changed to the sub-battery from the main battery when it is judged that a replacement operation of the main battery is started, a bias voltage is continually applied to a photoelectric converter even during the replacement operation of the main battery. Accordingly, it is not necessary to take time to stabilize an operation of the photoelectric converter and to detect an image for offset correction again when the replacement operation of the main battery is completed and the main power is turned on. Therefore, the start-up time after the replacement of the battery of the electronic cassette can be shortened.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

First Embodiment

Figure 1:
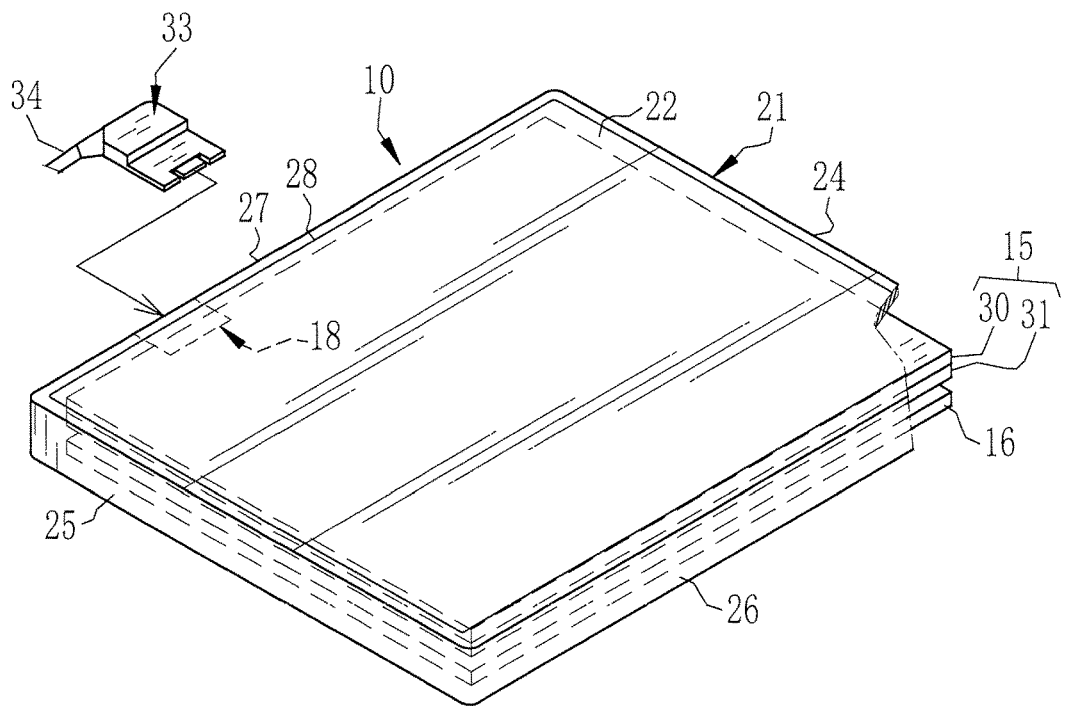
FIG. 1 is an external perspective diagram of an electronic cassette viewed from a front face side.
Figure 2:
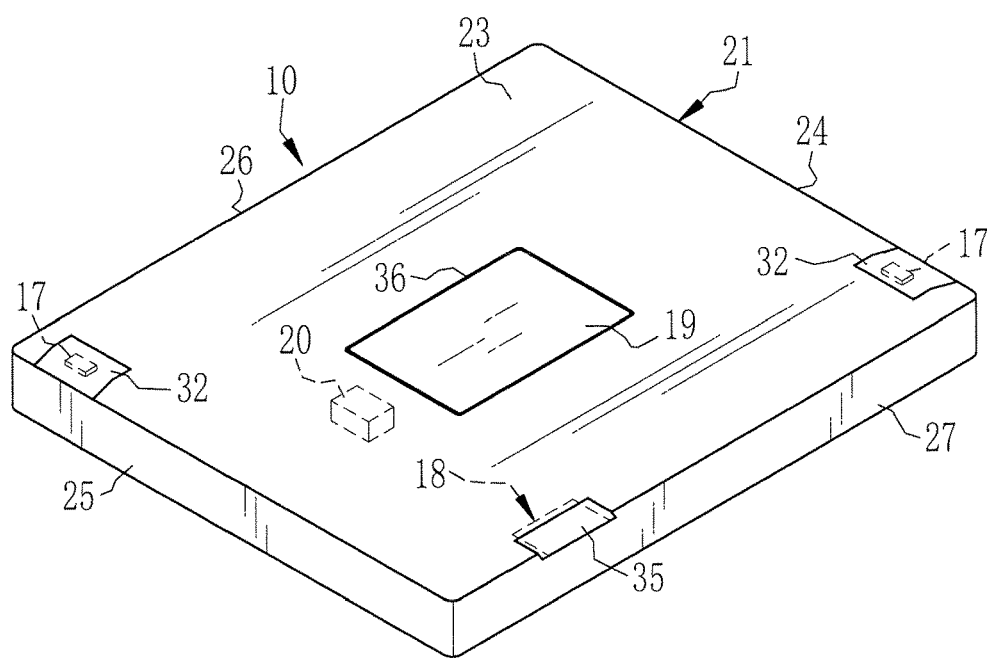
FIG. 2 is an external perspective diagram of the electronic cassette viewed from a back face side.

In FIG. 1 and FIG. 2, an electronic cassette 10 is used for example for medical radiography, and comprises an image detection unit 15, a circuit board 16, a radio communication unit 17, a female connector 18, a main battery 19, a sub-battery 20 and a housing 21 of portable type which contains these parts.

The housing 21 is constituted of a front face 22 where X-ray is incident on, a base face 23 opposite to the front face 22 and four side faces 24, 25, 26, 27, and has a cuboid shape. The housing 21 is formed for example of conductive resin, and functions as an electromagnetic shield which prevents invasion of electromagnetic noise to the electronic cassette 10 and emission of electromagnetic noise from the electronic cassette 10 to outside. For example, the housing 21 has the almost same size as that of a film cassette, an IP (Imaging Plate) cassette or a CR (Computed Radiography) cassette, and follows the international standard ISO (International Organization for Standardization) 4090:2001.

The electronic cassette 10 is detachably attached in a holder of an upright radiographing table or a decubitus radiographing table to keep a posture that an X-ray source irradiating X-ray and the front face 22 are facing each other. In addition, the electronic cassette 10 may be used alone for an object lying on a bed or an object who cannot move with his/her own strength such as an elderly person or an emergency case. Furthermore, in case the housing 21 has almost the same size as that of a film cassette, an IP cassette or a CR cassette, the electronic cassette 10 can be attached to existing photographing tables for these cassettes.

A rectangular opening is formed in the front face 22, and a transmission plate 28 is attached to the opening. The transmission plate 28 is formed of a carbon material which is lightweight and has high rigidity and radiolucency. In addition, in the housing 21, an indicator (not illustrated) such as an LED (Light Emitting Diode) is provided for indicating operating conditions of the electronic cassette 10 such as on/off of the main power, capacity of the main battery 19 and completion of photographing preparation.

The image detection unit 15 is composed of a scintillator 30 and a photo detection substrate 31. The scintillator 30 and the photo detection substrate 31 are laminated in order of the scintillator 30 and the photo detection substrate 31 from the front face 22 side where X-ray is incident on. The scintillator 30 has a fluorescent substance such as CsI:Tl (Thallium-activated Cesium Iodide) or GOS ($Gd_2O_2S$:Tb, Terbium-activated Gadolinium Oxysulfide), converts X-ray incident through the transmission plate 28 into visible light and emits it.

The photo detection substrate 31 detects visible light emitted from the scintillator 30 and converts it into an electric signal. The circuit board 16 controls drive of the photo detection substrate 31 and generates an X-ray image based on the electric signal output from the photo detection substrate 31.

The radio communication units 17 are provided one by one at the corner where the side face 25 intersects the side face 26 and at the corner where the side face 24 intersects the side face 27. The radio communication unit 17 is covered with a cover 32 formed of a nonconductive material such as a resin having radio wave permeability. The radio communication unit 17 performs radio communication with a control unit (not illustrated) which controls operation of the electronic cassette 10 and transmits variety of information such as an X-ray image. When the radio communication unit 17 is used, the electronic cassette 10 can be used without a cable, by being driven by electricity from the main battery 19.

The female connector 18 is provided in the side face 27, to enable a wired communication with the control unit. A male connector 33 is connected to the female connector 18. To the male connector 33, one end of a cable 34 is connected to establish a wired communication between the electronic cassette 10 and the control unit. The other end of the cable 34 is connected to a connector (not illustrated) to be connected to the control unit. The female connector 18 is protected by being covered with a lid 35 when the male connector 33 is not connected to it, for example at the time of using the wireless communication function.

The electronic cassette 10 receives not only variety of information but also electricity from the control unit through the female connector 18. When the female connector 18 and the male connector 33 are connected, the electronic cassette 10 is driven with electricity from the control unit.

The main battery 19 is composed of a rechargeable secondary battery. The main battery 19 supplies electricity to sections of the electronic cassette 10 through a power feeding unit 59 (refer to FIG. 3). In a central part of the base face 23, a battery loading unit 36 in which the main battery 19 is detachably loaded is provided. FIG. 2 illustrates the state that the main battery 19 is loaded in the battery loading unit 36. In addition, the battery loading unit 36 is provided with a well-known falling prevention/release mechanism (not illustrated) such as a lock mechanism and the unlock mechanism described in Japanese Patent Laid-Open Publication No. 2014-142355, to fix the main battery 19 to the battery loading unit 36 for preventing falling of the main battery 19 and release the fixation.

On/off of the main power of the electronic cassette 10 links to attachment/detachment of the main battery 19 to/from the battery loading unit 36. Specifically, the main power is turned off when the main battery 19 is detached from the battery loading unit 36, and is turned on when the main battery 19 is attached to the battery loading unit 36.

The sub-battery 20 is incorporated in the housing 21. The sub-battery 20 supplies electricity to a bias power circuit 50 (refer to FIG. 3) through the power feeding unit 59 in substitution for the main battery 19, when a replacement operation of the main battery 19 is started. The sub-battery 20 is composed of a rechargeable secondary battery like the main battery 19. The sub-battery 20 may be composed of a rechargeable storage element such as an electric double layer capacitor or a lithium ion capacitor.

Figure 3:
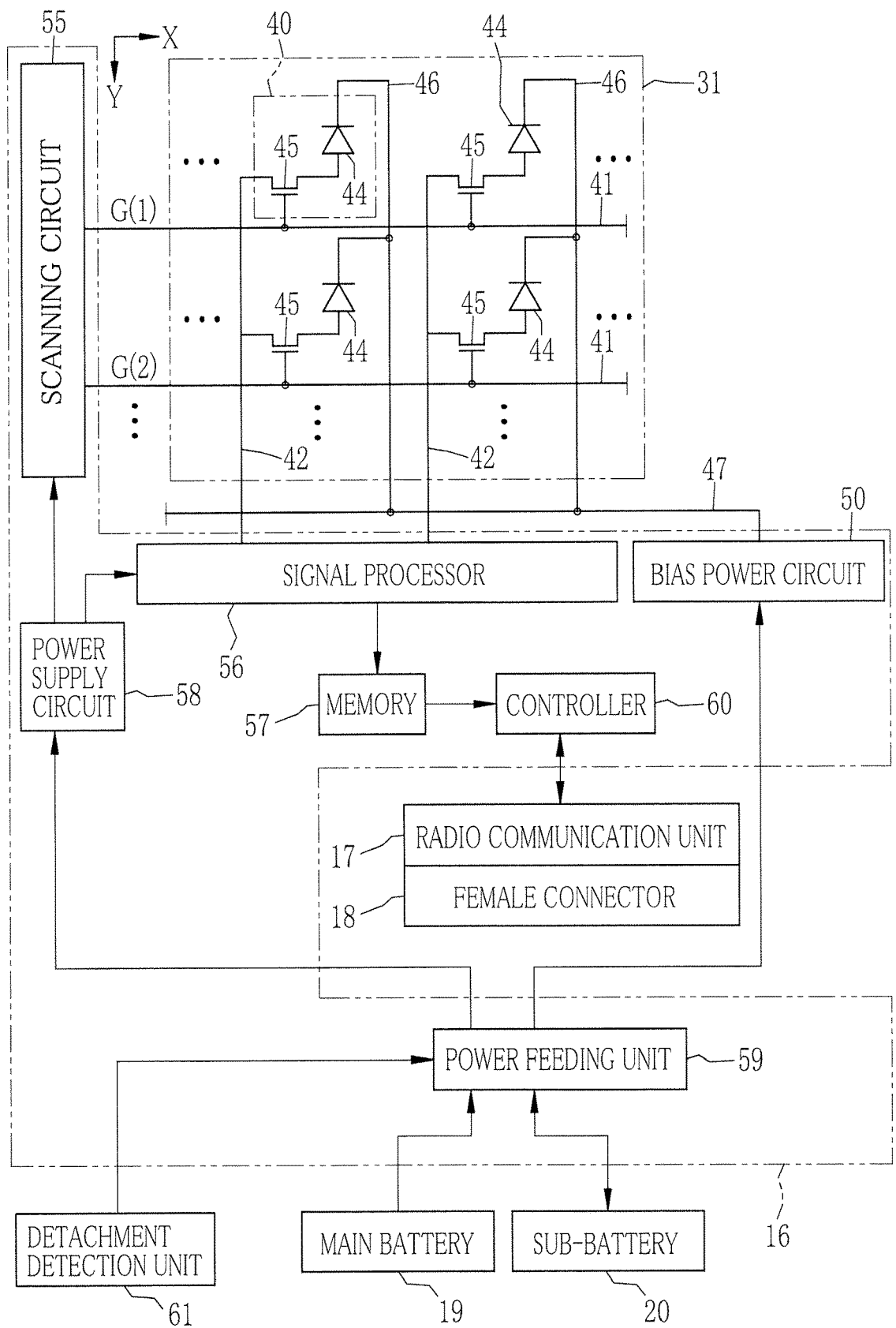
FIG. 3 is a block diagram of an electrical constitution of the electronic cassette.

In FIG. 3, pixels 40 arranged into a two-dimensional matrix of N-by-M array, N scanning lines 41 and M signal lines 42 are provided on a glass substrate (not illustrated) in the photo detection substrate 31. The N scanning lines 41 are arranged in Y direction along the column direction of the pixels 40 at a predetermined pitch, and extend in X direction along the line direction of the pixels 40. The M signal lines 42 extending in the Y direction are arranged in the X direction at a predetermined pitch. The scanning line 41 is orthogonal to the signal line 42, and the pixel 40 is provided corresponding to a crossing point of the scanning line 41 and the signal line 42. Note that N and M are integers no less than 2, for example, N, M~2000. In addition, the arrangement of the pixels 40 is not limited to the square arrangement of this embodiment, and may be a honeycomb arrangement.

As is generally known, the pixel 40 includes a photoelectric converter 44 which generates electric charge (electron-hole pair) by incidence of visible light and accumulates the charge and a TFT 45 which is a switching element. The photoelectric converter 44 has the structure that an upper electrode and a lower electrode are provided on upper and lower sides of a semiconductor layer producing electric charge. For example, the semiconductor layer is a PIN (p-intrinsic-n) type, an N-type layer is formed on the upper electrode side, and a P-type layer is formed on the lower electrode side. The TFT 45 has a gate electrode connected to the scanning line 41, a source electrode connected to the signal line 42, and a drain electrode connected to the lower electrode of the photoelectric converter 44.

A bias line 46 is connected to the upper electrode of the photoelectric converter 44. The provided bias lines 46 of the number (M) of rows of the pixels 40 are connected to a single bus line 47. The bus line 47 is connected to the bias power circuit 50. Through the bus line 47 and the bias line 46 which is the child line of the bus line 47, a positive bias voltage is applied to the upper electrode of the photoelectric converter 44 from the bias power circuit 50. By the application of the positive bias voltage, an electric field occurs in the semiconductor layer. The photoelectric converter 44 is used in a reverse bias state. The electron of the electron-hole pairs which occurred in the semiconductor layer by photoelectric conversion moves to the upper electrode and is absorbed in the bias line 46, and the positive hole moves to the lower electrode and is collected as electric charge.

In the circuit board 16, the above-mentioned bias power circuit 50, a scanning circuit 55, a signal processor 56, a memory 57, a power supply circuit 58, a power feeding unit 59 and a controller 60 for controlling these sections are provided.

The scanning circuit 55 is connected to the end of the each scanning line 41, and generates a gate pulse G (K) (K=1 to N) to drive the TFT 45. The scanning circuit 55 corresponds to a driving circuit, and the gate pulse G (k) corresponds to a drive voltage. The controller 60 drives the TFT 45 through the scanning circuit 55 to make the image detection unit 15 perform a pixel reset operation, an accumulation operation and an image reading operation. In the pixel reset operation, a dark electric charge is read from the pixel 40 for resetting (cancelling). In the accumulation operation, electric charge corresponding to a reached X-ray dose is accumulated in the pixel 40. In the image reading operation, the electric charge is read from the pixel 40.

In the pixel reset operation and the image reading operation, the scanning circuit 55 applies the gate pulse G (K) sequentially to the each scanning line 41, to turn on the TFTs 45 connected to the each scanning line 41 sequentially line by line. In the accumulation operation, since the gate pulse G (K) is not applied from the scanning circuit 55, the TFT 45 is in an off state.

The signal processor 56 is connected to the end of the each signal line 42. The signal processor 56 has an integral amplifier, a gain amplifier, a CDS (Correlated Double Sampling) circuit, a multiplexer and an A/D (Analog-to-Digital) converter (these are not illustrated).

The integral amplifier accumulates electric charge input from the signal line 42 and integrates it, and outputs an analog voltage value (image signal) corresponding to the integrated electric charge. The integral amplifier has an amplifier reset switch. When the amplifier reset switch is turned on, the electric charge accumulated in the integral amplifier is reset (canceled) In the pixel reset operation, the electric charge is reset without an image signal being output from the integral amplifier.

In the image reading operation, after an image signal corresponding to the electric charge is output from the integral amplifier, the amplifier reset switch is turned on and the electric charge is reset.

The gain amplifier amplifies the image signal output from the integral amplifier with a predetermined gain level. The CDS circuit applies a well-known correlative double sampling process to the image signal amplified by the gain amplifier, and removes a reset noise component of the integral amplifier from the image signal. The integral amplifier, the gain amplifier and the CDS circuit are provided for each of M lines of the signal line 42.

The multiplexer selects the CDS circuit of line 1 to line M sequentially line by line, and inputs the image signal output from the each CDS circuit to the A/D converter in a serial manner. The A/D converter applies an A/D conversion process to an input image signal, and output a digital image signal. The digital image signal output from the A/D converter is stored as an X-ray image in the memory 57.

The power supply circuit 58 supplies the gate pulse G (K) to the scanning circuit 55. In addition, the power supply circuit 58 supplies a drive voltage to the signal processor 56. Accordingly, the power supply circuit 58 corresponds to a first power supply circuit and a second power supply circuit. In addition, though illustration is omitted, the power supply circuit 58 supplies a drive voltage to other electric circuits such as the radio communication unit 17, the memory 57 and the controller 60.

The each battery 19, 20 and a detachment detection unit 61 are connected to the power feeding unit 59. The power feeding unit 59 supplies electricity from the main battery 19 or the sub-battery 20 to each section of the electronic cassette 10, such as the bias power circuit 50 and the power supply circuit 58. The power feeding unit 59 is composed of a DC (Direct Current)—DC converter which converts a DC voltage from the each battery 19, 20 into a voltage whose value is adapted to the section to which the voltage is supplied, a voltage stabilizer which stabilizes a value of the converted voltage, and so on. In addition, though illustration is omitted, since the female connector 18 is connected to the power feeding unit 59, when the female connector 18 and the male connector 33 are connected, the power feeding unit 59 receives electricity from the control unit through the female connector 18 and supplies the electricity from the control unit to each section.

The detachment detection unit 61 detects whether a detachment operation to detach the main battery 19 from the battery loading unit 36 is started. For example, the detachment detection unit 61 is composed of a micro switch or a photo sensor to detect whether the cancellation operation is applied to the falling prevention/release mechanism of the battery loading unit 36 by an operator. When the cancellation operation is applied to the falling prevention/release mechanism, the detachment detection unit 61 outputs a detection signal indicating the start of the detachment operation to the power feeding unit 59.

The controller 60 outputs the X-ray image stored in the memory 57 to the radio communication unit 17 or the female connector 18. In addition, the controller 60 receives variety of information from the control unit input through the radio communication unit 17 or the female connector 18, and controls each section depending on the received information. For example, the controller 60 receives a photography condition of the radiography, to change a gain level of the gain amplifier of the signal processor 56 depending on the photographing condition and control a start timing of the image reading operation depending on an X-ray irradiation time included in the photographing condition.

Figure 4:
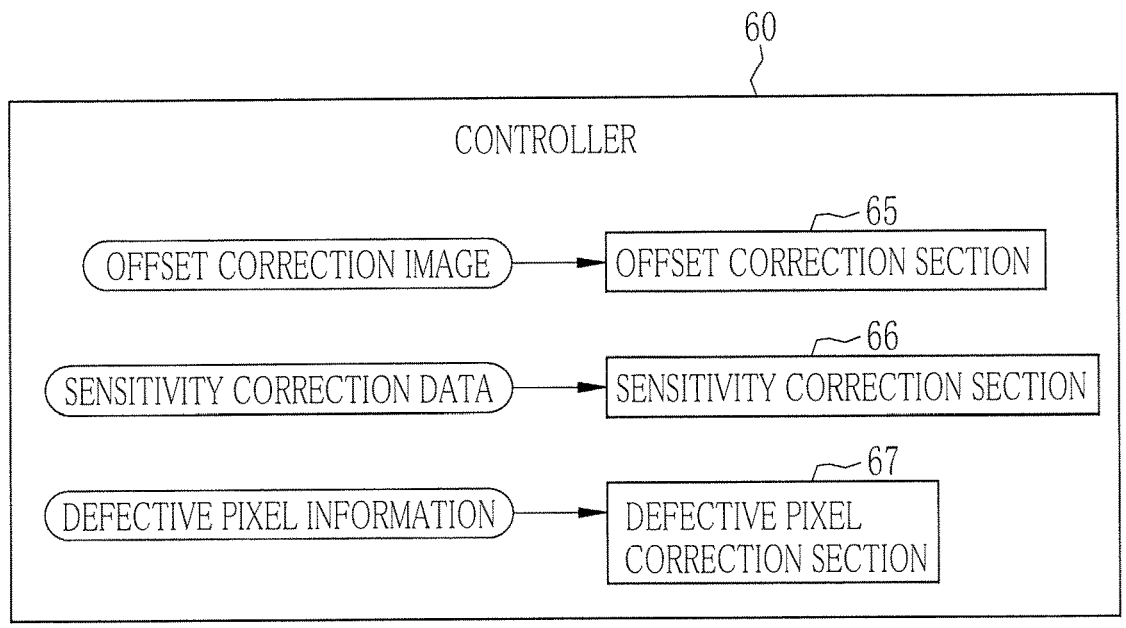
FIG. 4 is a schematic diagram of correction sections applying various corrections to an X-ray image, such as an offset correction.

In FIG. 4, correction sections 65, 66, 67 are provided in the controller 60, to apply various correction processing such as an offset correction, a sensitivity correction and a defective pixel correction to the X-ray image stored in the memory 57. The each correction section 65-67 accesses the memory 57 to read the X-ray image, applies various correction processing to the X-ray image, then writes the processed X-ray image back to the memory 57.

The offset correction section 65 deducts an image for offset correction, which is detected by the controller 60 making the image detection unit 15 perform the image reading operation while X-ray is not irradiated, from the X-ray image pixel by pixel basis. Accordingly, fixed pattern noise due to an individual difference of the signal processor 56 and a use environment of the electronic cassette 10 is removed from the X-ray image.

The sensitivity correction section 66 corrects an unevenness of the sensitivity of the photoelectric converter 44 of the each pixel 40, an unevenness of output characteristics of the signal processor 56 and so on based on sensitivity correction data. The defective pixel correction section 67 performs linear interpolation of a pixel level of a defect pixel with a pixel level of neighboring normal pixels 40, based on defect pixel information having an abnormal pixel level generated at the time of shipment or a periodic inspection. The X-ray image to which such the correction processes are applied are transmitted to the control unit through the radio communication unit 17 and the female connector 18. In addition, the image for offset correction, the sensitivity correction data and the defect pixel information are stored in an internal memory of the controller 60 which is not illustrated, and are read to the each correction section 65-67 at the time of the each correction process at appropriate timing.

Figure 5:
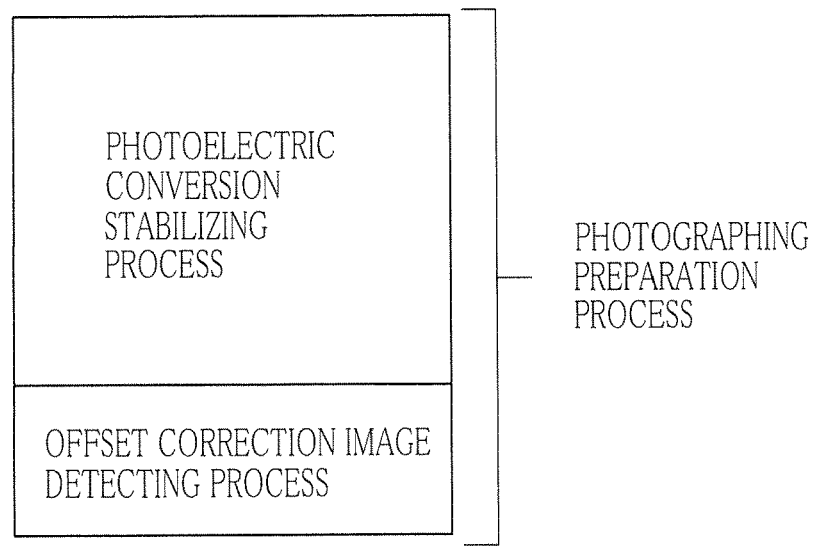
FIG. 5 is a schematic diagram of a photographing preparation process.

In FIG. 5, the controller 60 makes the image detection unit 15 perform a photographing preparation process when the bias power circuit 50 starts application of the bias voltage to the photoelectric converter 44, for example when the main battery 19 is attached to the battery loading unit 36 and the main power of the electronic cassette 10 is turned on at the time of start-up of a medical facility. The photographing preparation process is for making the electronic cassette 10 be in the state that the photographing preparation is completed and the radiography is possible. The photographing preparation process mainly includes a stabilization process of the operation of the photoelectric converter 44 (photoelectric conversion stabilizing process) and a process to make the image detection unit 15 detect an image for offset correction (offset correction image detecting process).

The photoelectric conversion stabilizing process is performed for the purpose of detecting an accurate image for offset correction, because an image for offset correction which reflects an use condition of the electronic cassette 10 accurately may not be obtained when the image for offset correction is detected before operation of the photoelectric converter 44 becomes stabilized after the main power is turned on and the application of bias voltage to the photoelectric converter 44 from the bias power circuit 50 is re-started. Specifically, in the photoelectric conversion stabilizing process, the image detection unit 15 is not operated and the offset correction image detecting process is prohibited until operation of the photoelectric converter 44 is stabilized. For example, the photoelectric conversion stabilizing process takes a time more than half of the time required for whole of the photographing preparation process.

The offset correction image detecting process is performed after the photoelectric conversion stabilizing process. For example, when the main power is turned on at the time of start-up of a medical facility, the offset correction image detecting process is performed because a use condition of the electronic cassette 10 might have changed since the time of former detection of the image for offset correction. In the offset correction image detecting process, the image reading operation is performed after a dark electric charge is reset in the pixel reset operation, to prevent that a dark electric charge component is superimposed on the image for offset correction.

In addition, the photographing preparation process further includes a process to activate the radio communication unit 17 and establish a wireless communication with the control unit, an initialization process of the scanning circuit 55, the signal processor 56, the memory 57 and so on. These processes are carried out parallel to the photoelectric conversion stabilizing process.

Figure 6:
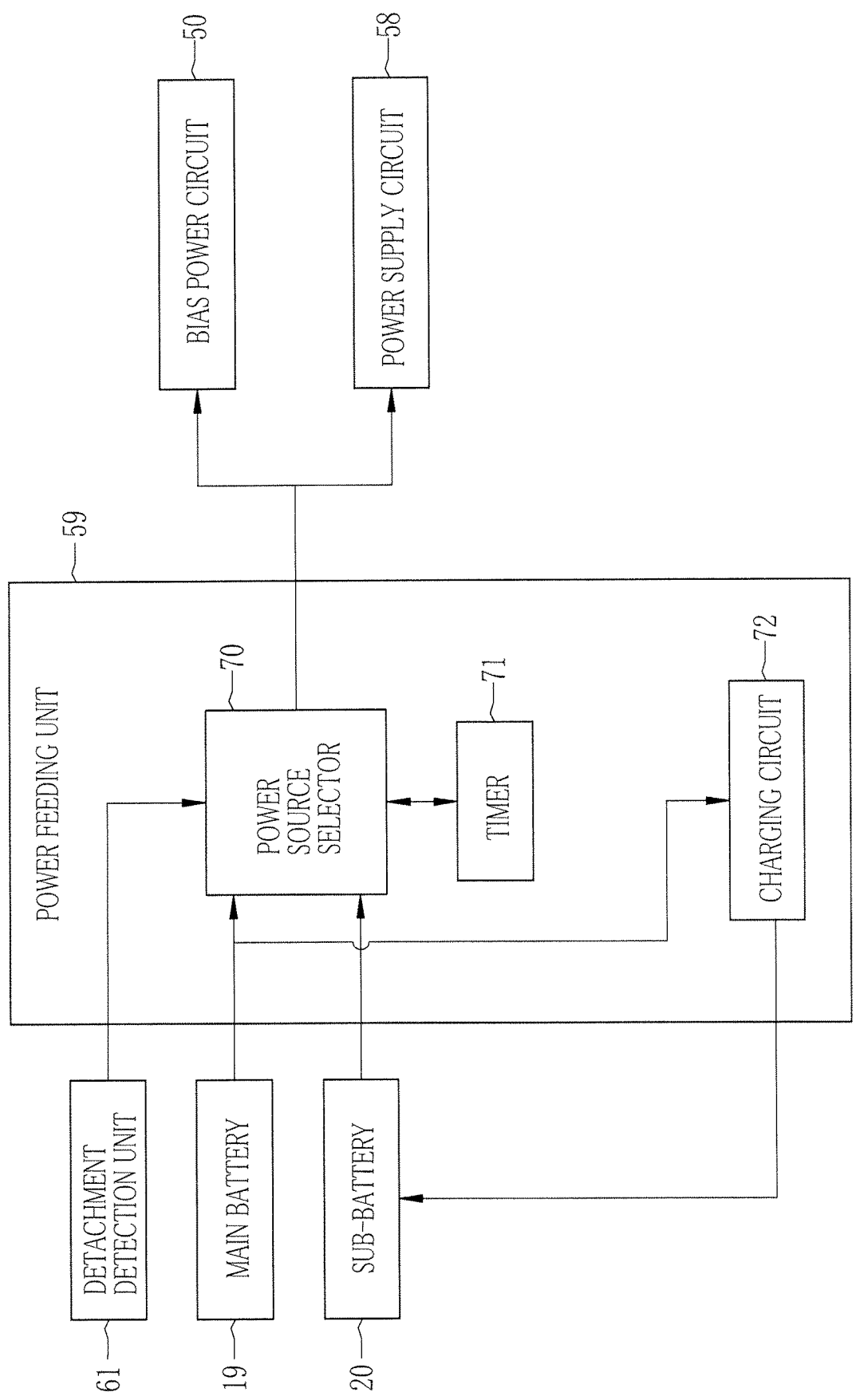
FIG. 6 is a block diagram of a power feeding unit.

As illustrated in FIG. 6, the power feeding unit 59 comprises a power source selector 70, a timer 71 and a charging circuit 72. A detection signal is input into power the source selector 70 from the detachment detection unit 61. The power source selector 70 changes a power source for the bias power circuit 50, the power supply circuit 58 and so on depending on the detection signal, by switching between the each battery 19, 20.

The timer 71 clocks a second elapsed time TP2 (refer to FIG. 10 and FIG. 11) after the power source selector 70 changes the power source to the sub-battery 20. Accordingly, the timer 71 corresponds to a second timer. When the second elapsed time TP2 reached a predetermined second set time TS2 (refer to FIG. 10 and FIG. 11), the timer 71 outputs a notification signal indicating this state to the power source selector 70. The second set time TS2 is an enough time from the start to the end of a replacement operation of the main battery 19 (e.g., five minutes).

The charging circuit 72 receives the electricity from the main battery 19 and charges the sub-battery 20. While the main battery 19 is attached to the battery loading unit 36, the charging circuit 72 operates. When sub-battery 20 was in a condition of the full charge, charging circuit 72 stops charge of sub-battery 20. In addition, though illustration is omitted, the charging circuit 72 has a function to receive the electricity from the control unit through the female connector 18 and charge the main battery 19.

Figure 7:
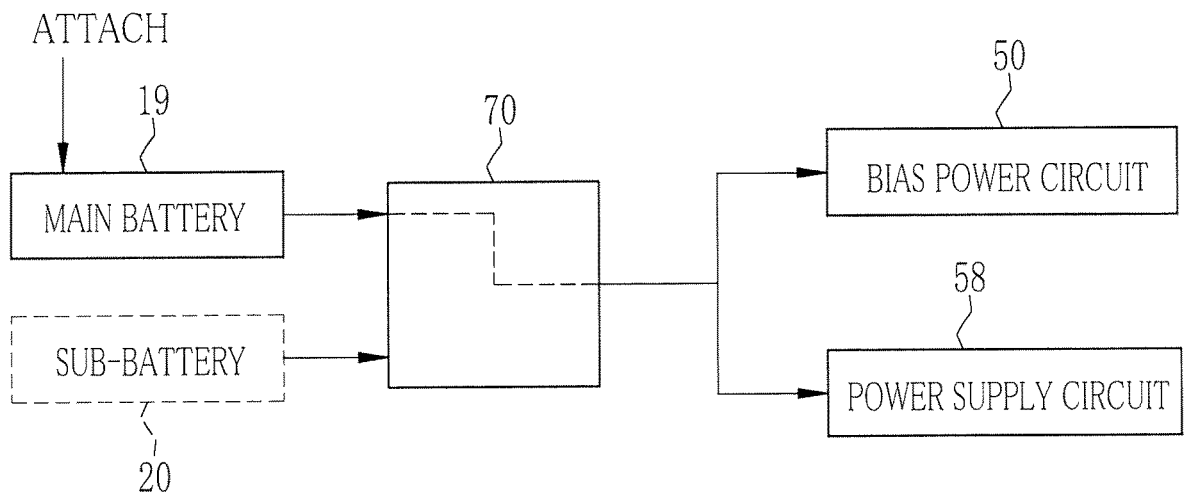
FIG. 7 is a schematic diagram indicating a case of supplying electricity from a main battery.

As illustrated in FIG. 7, when the main battery 19 is attached to the battery loading unit 36 and the main power is turned on, the power source selector 70 selects the main battery 19 as the power source and make the main battery 19 supply electricity to the bias power circuit 50, the power supply circuit 58 and so on.

Figure 8:
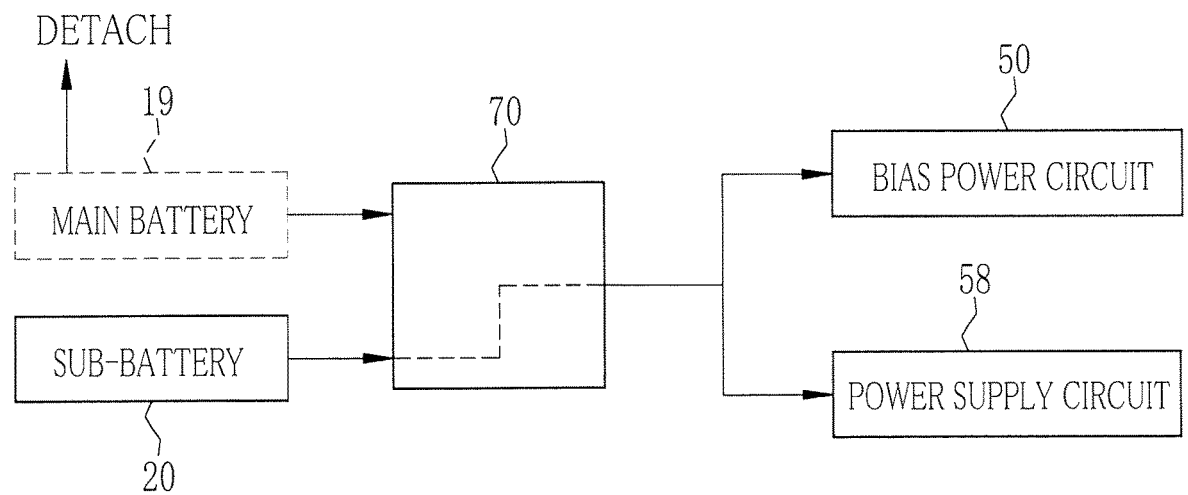
FIG. 8 is a schematic diagram indicating a case of supplying electricity from a sub-battery.

In addition, the power source selector 70 judges whether a replacement operation of the main battery 19 is started. As illustrated in FIG. 8, when the power source selector 70 judges that the detachment operation of the main battery 19 is started (the replacement operation is started), the power source selector 70 changes the power source from the main battery 19 to the sub-battery 20 and make the sub-battery 20 supply electricity to the bias power circuit 50, the power supply circuit 58 and so on.

When the main battery 19 runs short and is to be exchanged, a release operation of the falling prevention/release mechanism of the battery loading unit 36 is executed to detach the main battery 19 from the battery loading unit 36. Then the removed main battery 19 is charged with an exclusive battery charger (not illustrated), and another main battery 19 which has been charged is loaded in the battery loading unit 36. In other words, the replacement operation of the main battery 19 is started from the release operation of the falling prevention/release mechanism of the battery loading unit 36.

Accordingly, in this embodiment, the power source selector 70 judges that the replacement operation of main battery 19 is started when the release operation of the falling prevention/release mechanism of the battery loading unit 36 is executed, then changes the power source to the sub-battery 20 as illustrated in FIG. 8. Therefore, for example at an ending time of the medical facility when the electronic cassette 10 has not been activated for certain amount of time (at least longer than the second set time TS2) and the main battery 19 is removed from the battery loading unit 36, in other words, even in case that the main battery 19 is removed for an intention except the exchange of the main battery 19, the power source is changed to the sub-battery 20 by the power source selector 70 as illustrated in FIG. 8.

The power source selector 70 continues to supply of the electricity from sub-battery 20 as illustrated in FIG. 8 till the second elapsed time TP2 reaches the second set time TS2 (TP2<TS2). And when the second elapsed time TP2 reaches the second set time TS2 (TP2=TS2) and the notification signal indicating this state is input by the timer 71, the power source selector 70 stops the supply of the electricity from the sub-battery 20. In addition, when the main battery 19 is attached to the battery loading unit 36 and the main power is turned on while the sub-battery 20 supplies the electricity (before the second elapsed time TP2 reaches the second set time TS2), the power source selector 70 changes a power source to the main battery 19 as illustrated in FIG. 7.

Next, an operation of the above-described embodiment is explained with reference to a flow chart of FIG. 9 and timing charts of FIG. 10 and FIG. 11. Note that the explanation starts from the state that the main battery 19 is already attached and the main power is turned on, and all sections are activated by the electricity supplied from the main battery 19.

Figure 9:
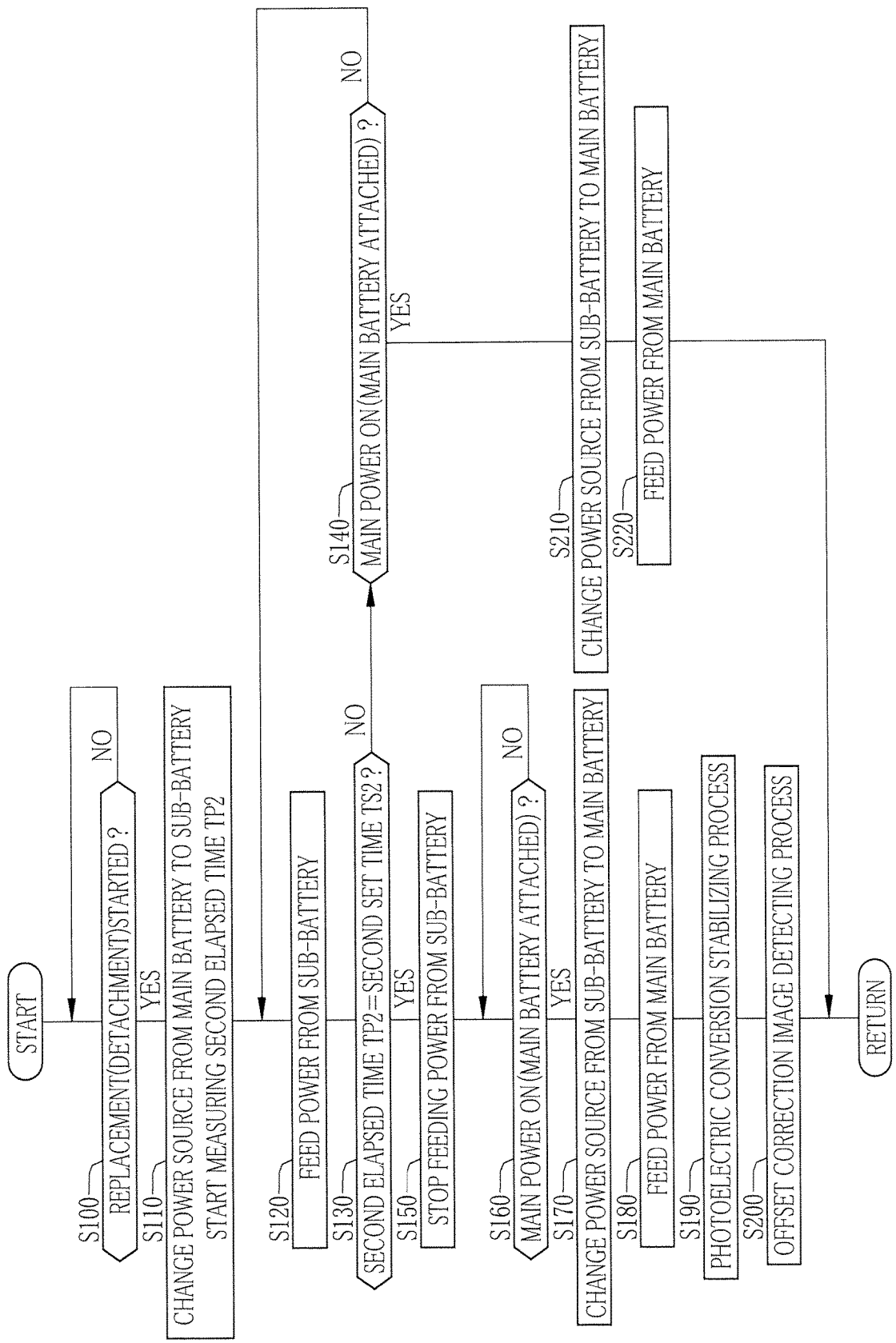
FIG. 9 is a flow chart of an operation of the electronic cassette.
Figure 10:
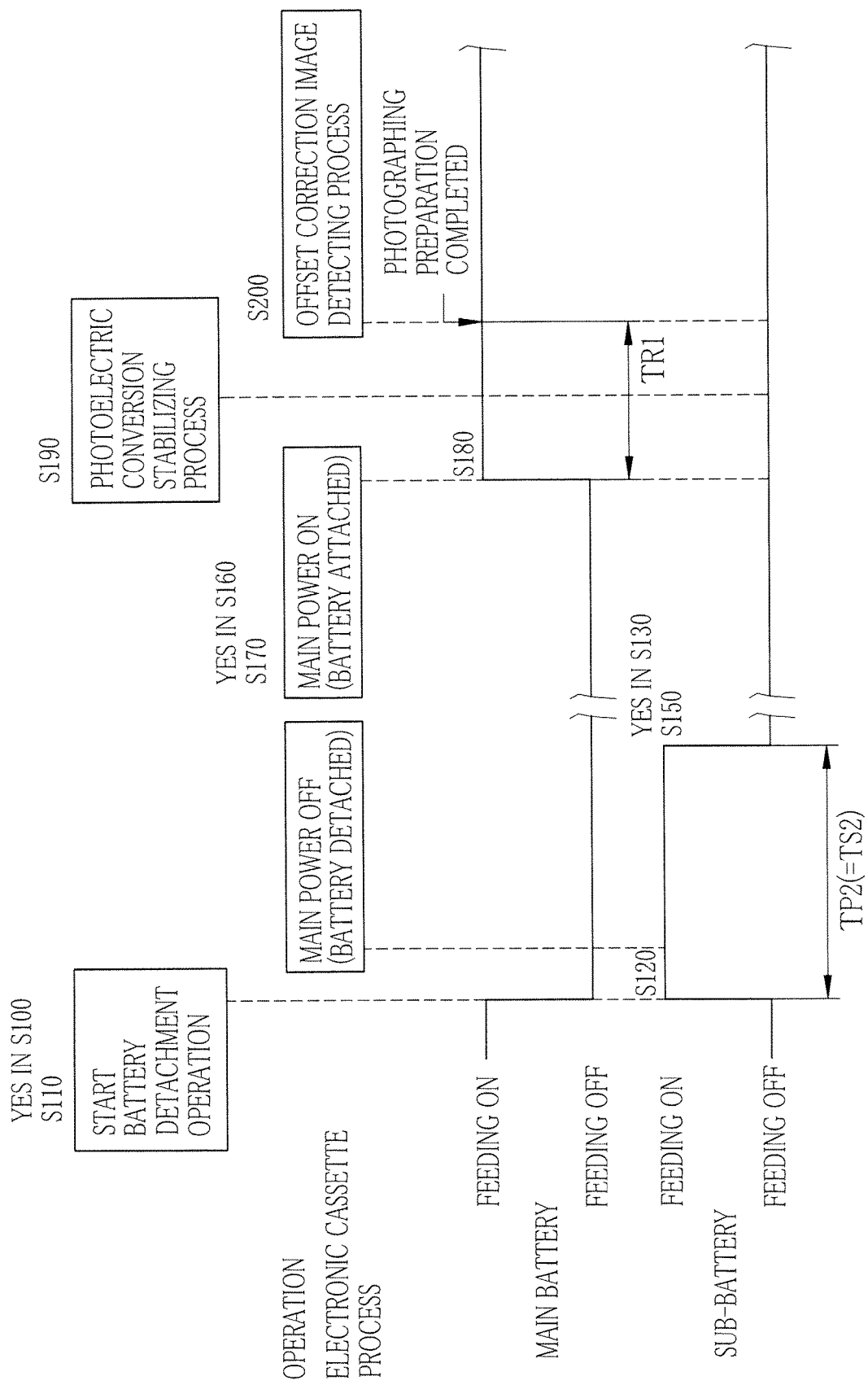
FIG. 10 is a timing chart indicating an operation of the electronic cassette in case that the main battery is removed for a purpose except an exchange of the main battery.
Figure 11:
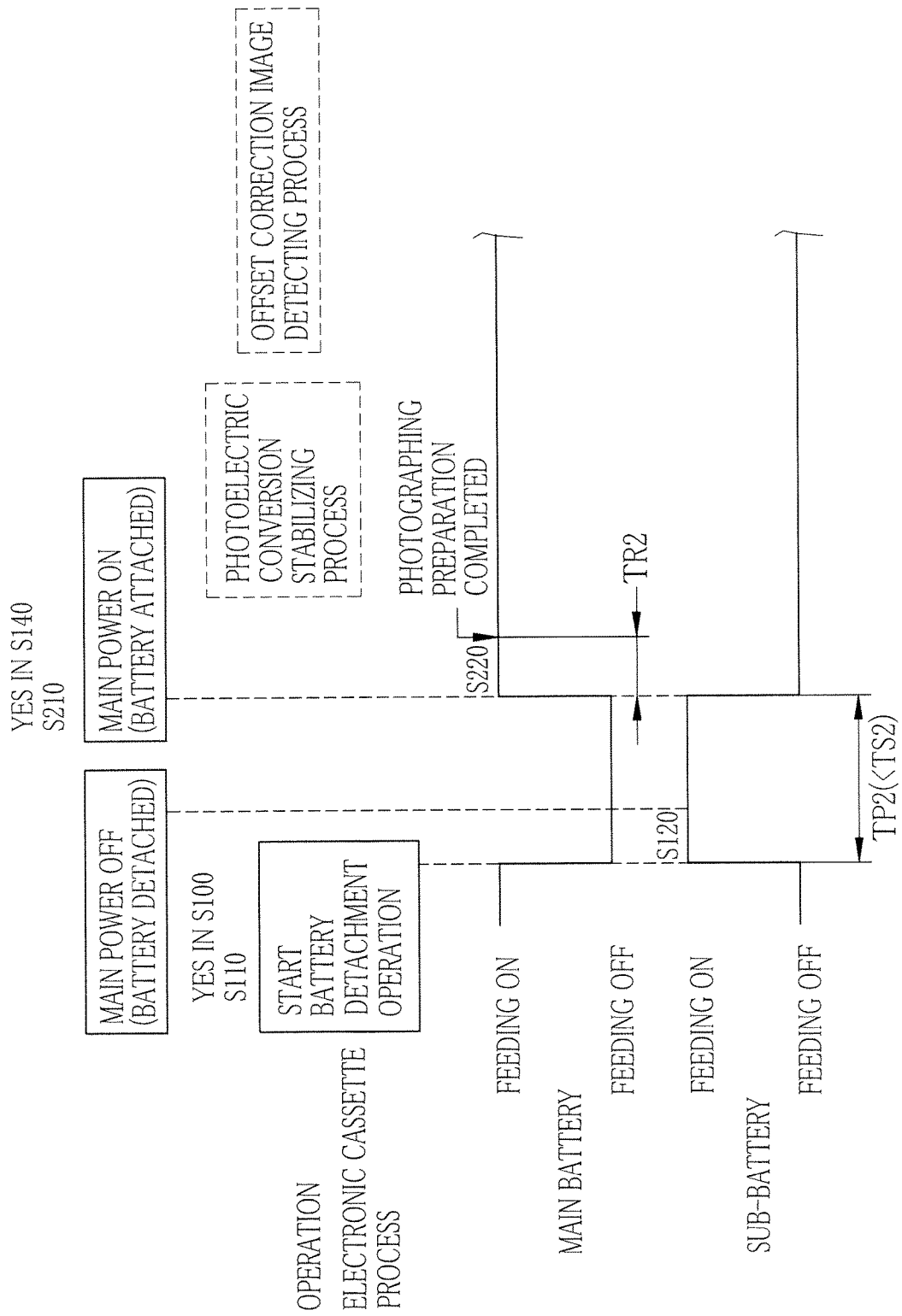
FIG. 11 is a timing chart indicating an operation of the electronic cassette in case that the main battery is removed for exchanging the main battery.

In step S100 of FIG. 9 to FIG. 11, the power source selector 70 monitors the detection signal from the detachment detection unit 61, and judges whether the replacement operation (detachment operation) of the main battery 19 is started. While the replacement operation is not started, power supply from the main battery 19 to each section is continued (No in step S100).

When an operator operates the falling prevention/release mechanism of battery loading unit 36 for the release operation, the detection signal is input into the power source selector 70 from the detachment detection unit 61. The power source selector 70 judges that the replacement operation of the main battery 19 is started, upon receiving the detection signal (YES in step S100). Then the power source selector 70 changes the power source from the main battery 19 to the sub-battery 20. In addition, at the same timing, the clock of the second elapsed time TP2 is started with the timer 71 (step S110). In this way, electricity is supplied to the bias power circuit 50, the power supply circuit 58 and so on from the sub-battery 20 (step S120).

When the attachment of the main battery 19 to the battery loading unit 36 and the turning on of the main power are not completed before the second elapsed time TP2 reaches the second set time TS2 (No in steps S130 and S140), the supply of the electricity from the sub-battery 20 is continued until the second elapsed time TP2 reaches the second set time TS2. Note that when electricity is supplied from the sub-battery 20 and the sub-battery 20 runs short, the sub-battery 20 is charged with electricity from the main battery 19 through the charging circuit 72.

When the second elapsed time TP2 reaches the second set time TS2 (YES in step S130), the notification signal indicating this state is output from the timer 71 to the power source selector 70. Then the supply of the electricity from the sub-battery 20 is stopped by the power source selector 70 (step S150). Therefore, as for the cases that the attachment of the main battery 19 and the turning on of the main power are not completed before the second elapsed time TP2 reaches the second set time TS2, for example that the main battery 19 is removed for an intention except the exchange of the main battery 19, the application of the bias voltage to the photoelectric converter 44 is stopped because the electricity to the bias power circuit 50 is no longer supplied from either of the batteries 19 and 20.

When the main battery 19 is loaded and the main power is turned on in the state that the application of the bias voltage to the photoelectric converter 44 is stopped (YES in step S160), the power source is changed to the main battery 19 from the sub-battery 20 by the power source selector 70 (step S170), and electricity is supplied to the bias power circuit 50, the power supply circuit 58 and so on from the main battery 19 (step S180). In this case, since the application of the bias voltage to the photoelectric converter 44 had been stopped, the photoelectric conversion stabilizing process and the offset correction image detecting process are performed by the controller 60 (steps S190 and S200).

When the attachment of the main battery 19 and the turning on of the main power are completed before the second elapsed time TP2 reaches the second set time TS2 (NO in step S130, YES in step S140), the power source is changed to the main battery 19 from the sub-battery 20 by the power source selector 70 (step S210), and electricity is supplied to the bias power circuit 50, the power supply circuit 58 and so on from the main battery 19 (step S220), as same as steps S170 and S180.

In this case also, as well as the case that the second elapsed time TP2 reaches the second set time TS2 (YES in step S130), and the main battery 19 is loaded and the main power is turned on (YES in step S160), the power source is sequentially changed from the main battery 19 to the sub-battery 20 when the main battery 19 is detached, and from the sub-battery 20 to the main battery 19 when the main battery 19 is attached. However, the supply of the electricity to the bias power circuit 50 is continued by the each battery 19, 20, and the bias voltage continues being applied to the photoelectric converter 44 without a break. Accordingly, in this case the photoelectric conversion stabilizing process and the offset correction image detecting process are not performed. Therefore, a start-up time TR2 of this case illustrated in FIG. 11 is largely shortened from a start-up time TR1 illustrated in FIG. 10 in which the photoelectric conversion stabilizing process and the offset correction image detecting process are performed.

Accordingly, even when the main battery 19 is changed in the middle of radiography, the radiography can be re-started relatively in a short time, without waiting for a long time. Therefore, photography efficiency can be improved and a stress to an object can be reduced.

Even in case the main battery 19 is removed for an intention except the exchange of the main battery 19, when the attachment of the main battery 19 and the turning on of the main power are completed before the second elapsed time TP2 reaches the second set time TS2, the photoelectric conversion stabilizing process and the offset correction image detecting process are not performed and the start-up time becomes TR2. Therefore, there is the secondary effect to be able to restart radiography in a short time even when detachment/attachment of the main battery 19 is carried out for saving electric power.

Since the sub-battery 20 is used for power supply alternatively only during the replacement operation of the main battery 19, it is enough that the sub-battery 20 has a capacity to supply electricity at least during a period from a start to a completion of the replacement operation of the main battery 19. Therefore, the sub-battery 20 can be very small in capacity and size in comparison with the main battery 19.

Since the main battery 19 needs to be removed for exchanging the main battery 19, an overlook of a start timing of the replacement operation of the main battery 19 can be prevented by detecting a start of the detachment operation of the main battery 19 as the start of the replacement operation of the main battery 19.

In case the power source is changed to the sub-battery 20 after the main battery 19 is removed from the battery loading unit 36 and the supply of the electricity from the main battery 19 is completely cut off, an instantaneous interruption of power supply occurs. To prevent the instantaneous interruption of power supply, in this embodiment, a start of the detachment operation of the main battery 19 is detected to change the power source to the sub-battery 20 before the supply of the electricity from the main battery 19 is completely cut off.

In addition, since the timer 71 clocks the second elapsed time TP2 after the power source is changed to the sub-battery 20 and the supply of the electricity from sub-battery 20 is stopped when the second elapsed time TP2 reaches the second set time TS2, a battery power waste can be prevented.

Note that the timer 71 can be omitted. In case the timer 71 is not provided, the sub-battery 20 can play a role as the timer 71, by using the sub-battery 20 having a capacity which makes a discharging time from the full charge state to the zero state agree with the second set time TS2, and the charging circuit 72 charging the sub-battery 20 only when the capacity of the sub-battery 20 becomes zero.

Second Embodiment

In the first embodiment mentioned above, attachment and detachment of the main battery 19 to and from the battery loading unit 36 link on/off of the main power of the electronic cassette 10. However, a main power switch 80 may be provided in the housing 21 for operating on/off of the main power.

Figure 12:
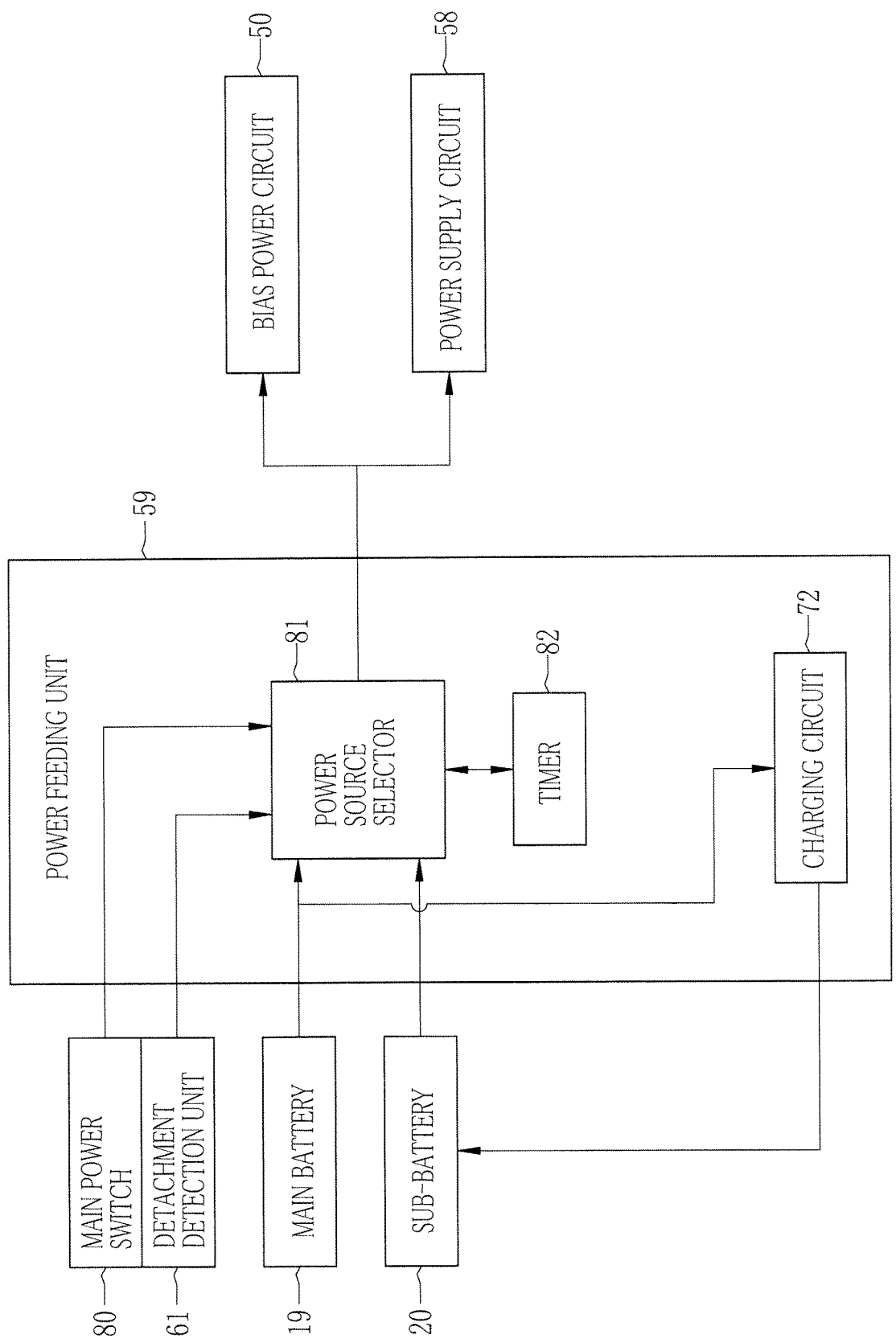
FIG. 12 is a block diagram of a power feeding unit of a second embodiment provided with a main power switch.

In this case, as illustrated in FIG. 12, an operation signal of the main power switch 80 is input into a power source selector 81, in addition to the detection signal of the detachment detection unit 61. For exchanging the main battery 19, at first the main power switch 80 is turned off, the main battery 19 is removed from the battery loading unit 36 thereafter.

In addition, in this embodiment, a timer 82 times a first elapsed time TP1 (refer to FIG. 14 and FIG. 15) after the main power switch 80 is turned off, in addition to the second elapsed time TP2 of the first embodiment mentioned above.

In other words, the timer 82 corresponds to the first timer and the second timer. When the first elapsed time TP1 reached a predetermined first set time TS1 (refer to FIG. 14 and FIG. 15), the timer 82 outputs a notification signal indicating this state to the power source selector 81. Note that the first set time TS1 is no more than the second set time TS2 of the first embodiment.

When the main power switch 80 is turned on, the power source selector 81 selects the main battery 19 as the power source and makes the main battery 19 supply electricity to the bias power circuit 50, the power supply circuit 58 and so on. After the main power switch 80 is turned off, the power source selector 81 continues to supply of the electricity from the main battery 19 until the first elapsed time TP1 reaches the first set time TS1. In addition, the power source selector 81 stops the supply of the electricity from the main battery 19 after the first elapsed time TP1 reaches the first set time TS1, even when the detection signal is not input from the detachment detection unit 61.

Furthermore, when the detection signal is input from the detachment detection unit 61 before the first elapsed time TP1 reaches the first set time TS1, the power source selector 81 judges that the replacement operation of the main battery 19 is started, and change the power source to the sub-battery 20 from the main battery 19.

Next, an operation of this embodiment is explained with reference to a flow chart of FIG. 13 and timing charts of FIG. 14 and FIG. 15. Note that the explanation starts from the state that the main power switch 80 is turned on, and all sections are activated by the electricity supplied from the main battery 19.

Figure 13:
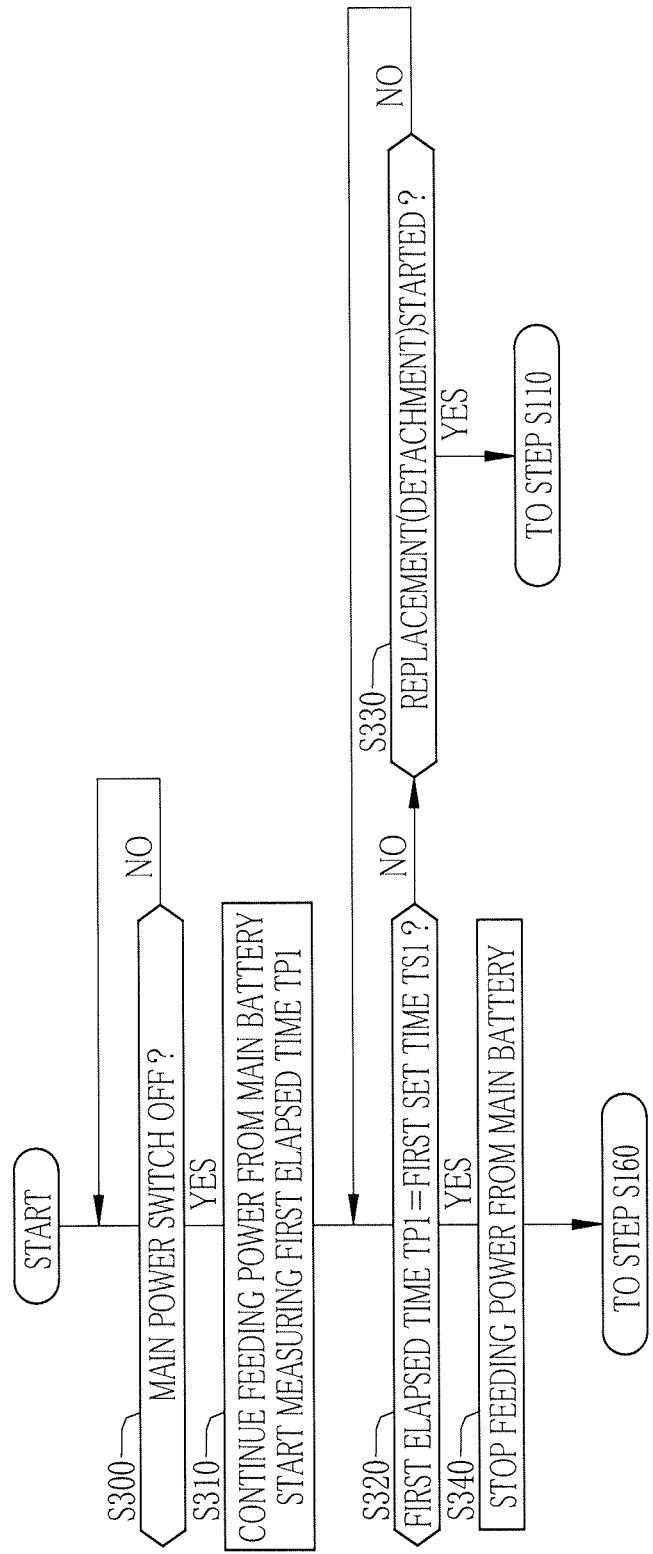
FIG. 13 is a flow chart of an operation of an electronic cassette of the second embodiment.
Figure 14:
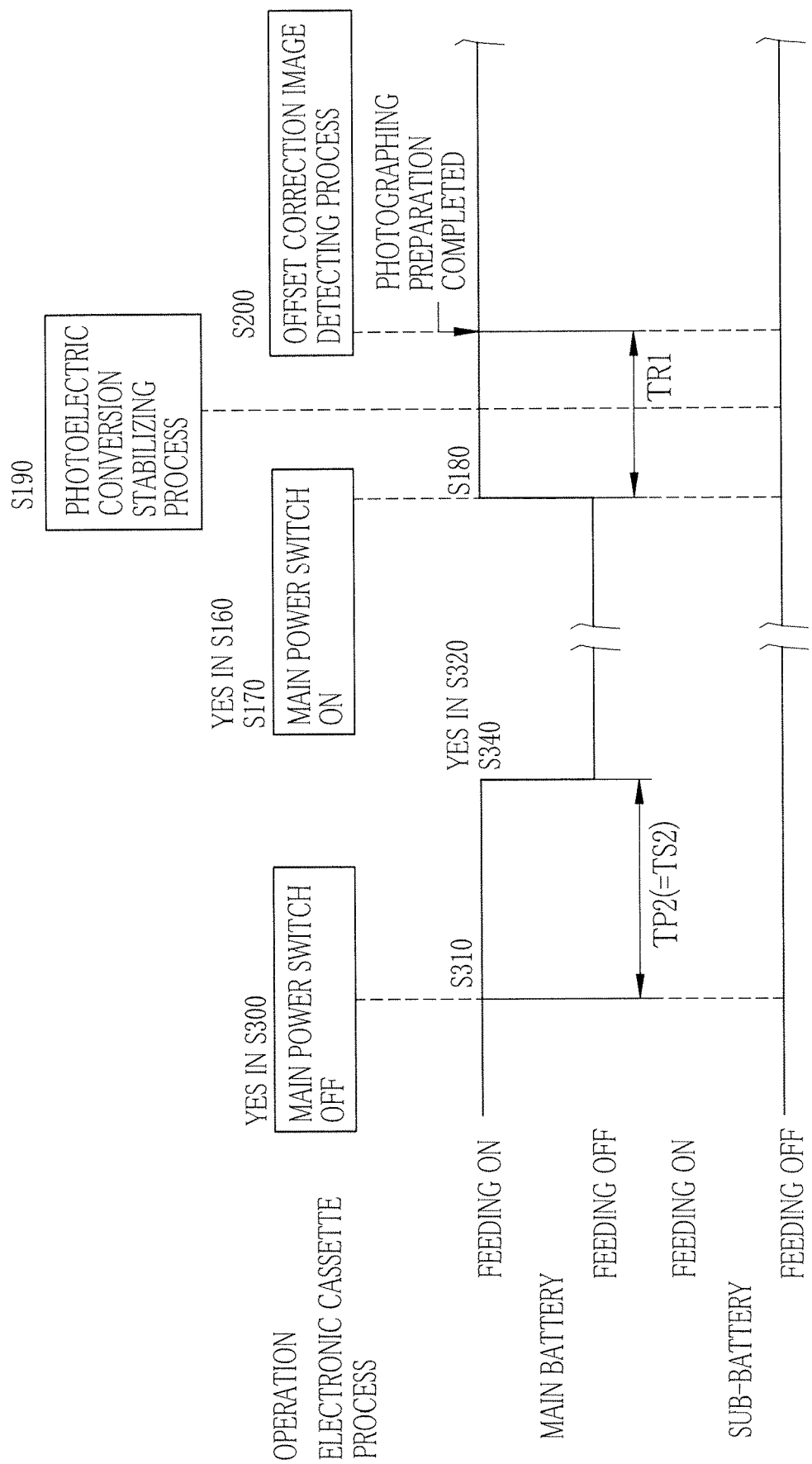
FIG. 14 is a timing chart indicating an operation of the electronic cassette in case that the main power switch is turned off for a purpose except an exchange of the main battery in the second embodiment.
Figure 15:
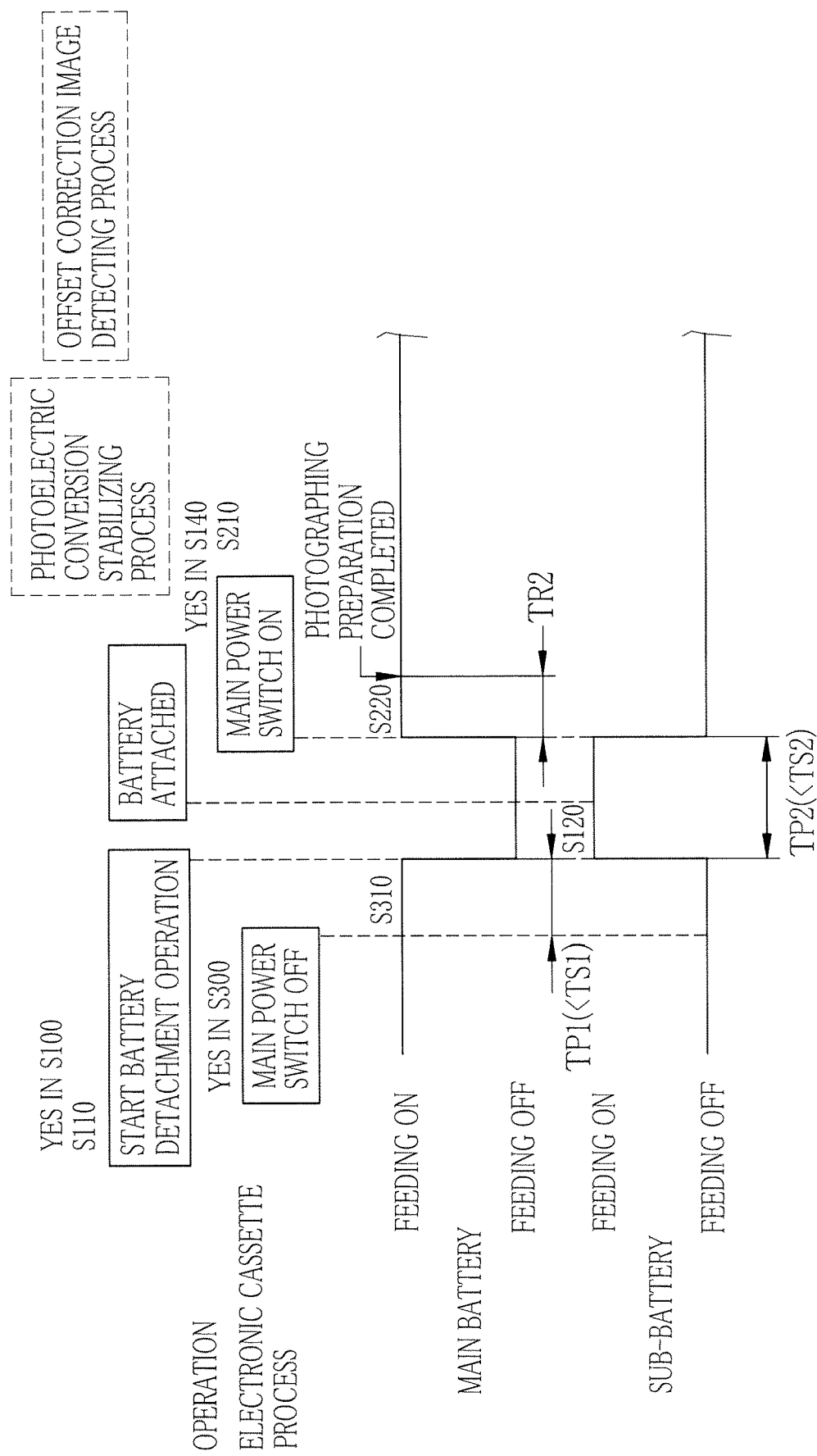
FIG. 15 is a timing chart indicating an operation of the electronic cassette in case that the main power switch is turned off for exchanging the main battery in the second embodiment.

In step S300 of FIG. 13 to FIG. 15, the power source selector 81 judges whether the main power switch 80 is turned off. In the first embodiment mentioned above, when the detachment operation of the main battery 19 is started, the power source is changed to the sub-battery 20 from the main battery 19 by the power source selector 70. However, in this embodiment, even when the main power switch 80 is turned off (YES in step S300), supply of the electricity from the main battery 19 is continued by the power source selector 81. In addition, timing of the first elapsed time TP1 is started concurrently by the timer 81. Accordingly, electricity is supplied continually from the main battery 19 to the bias power circuit 50, the power supply circuit 58 and so on (step S310).

When the detection signal is not input from the detachment detection unit 61 before the first elapsed time TP1 reaches the first set time TS1, in other words, when the detachment operation of the main battery 19 is not started (NO in steps S320 and S330), the supply of the electricity from the main battery 19 is continued until the first elapsed time TP1 reaches the first set time TS1.

When the first elapsed time TP1 reaches the first set time TS1 (YES in step S320), a notification signal indicating this state is output from the timer 82 to the power source selector 81. Then the supply of the electricity from the main battery 19 is stopped by the power source selector 81 (step S340). Therefore, as for the cases that the detection signal is not input from the detachment detection unit 61 before the first elapsed time TP1 reaches the first set time TS1, for example that the main power switch 80 is turned off for an intention except the exchange of the main battery 19, the application of the bias voltage to the photoelectric converter 44 is stopped because the electricity to the bias power circuit 50 is no longer supplied from either of the batteries 19 and 20. About the subsequent processes, description is omitted because it is the basically same to step S160 and subsequent processes of the first embodiment mentioned above, though a trigger of turning the main power on is changed to the turning on of the main power switch 80 from the attachment of the main battery 19.

When the detection signal is input from the detachment detection unit 61 before the first elapsed time TP1 reaches the first set time TS1, in other words, when the detachment operation of the main battery 19 is started (NO in step S320 and YES in step S330), the processing is transferred to step S110 of the first embodiment mentioned above. In other words, the power source selector 81 changes the power source from the main battery 19 to the sub-battery 20, and makes the sub-battery 20 supply electricity to the bias power circuit 50, the power supply circuit 58 and so on. About the subsequent processes, description is omitted because it is the basically same to step S110 and subsequent processes of the first embodiment mentioned above, though a trigger of turning the main power on is changed to the turning on of the main power switch 80 from the attachment of the main battery 19.

Also in this embodiment, the supply of the electricity to the bias power circuit 50 is continued by the each battery 19, 20, and the bias voltage continues being applied to the photoelectric converter 44 without a break. Accordingly, the photoelectric conversion stabilizing process and the offset correction image detecting process are not needed. Therefore, a start-up time TR2 illustrated in FIG. 15 is largely shortened from the start-up time TR1 illustrated in FIG. 14.

In addition, when the main power switch 80 is turned off for an intention except the exchange of the main battery 19 as illustrated in FIG. 14, the sub-battery 20 does not operate. Therefore, since using frequency of the sub-battery 20 can be reduced in comparison with the first embodiment in which the sub-battery 20 operates even when the main power switch 80 is turned off for an intention except the exchange of the main battery 19, degradation of the sub-battery 20 can be suppressed. Unlike the main battery 19 which can be replaced with a new one immediately after being deteriorated, the sub-battery 20 is provided in the housing 21 thus it cannot be replaced or repaired easily. Therefore, it is important that a frequency of troublesome maintenance such as exchange or repair of the sub-battery 20 is reduced by suppressing the degradation of the sub-battery 20.

Third Embodiment

In the embodiments mentioned above, upon detecting a start of the detachment operation of the main battery 19, it is judged that the replacement operation of the main battery 19 is started. However, in case the main power switch 80 is provided like in the second embodiment mentioned above, it may be judged that the replacement operation of the main battery 19 is started when the main power switch 80 is turned off.

Figure 16:
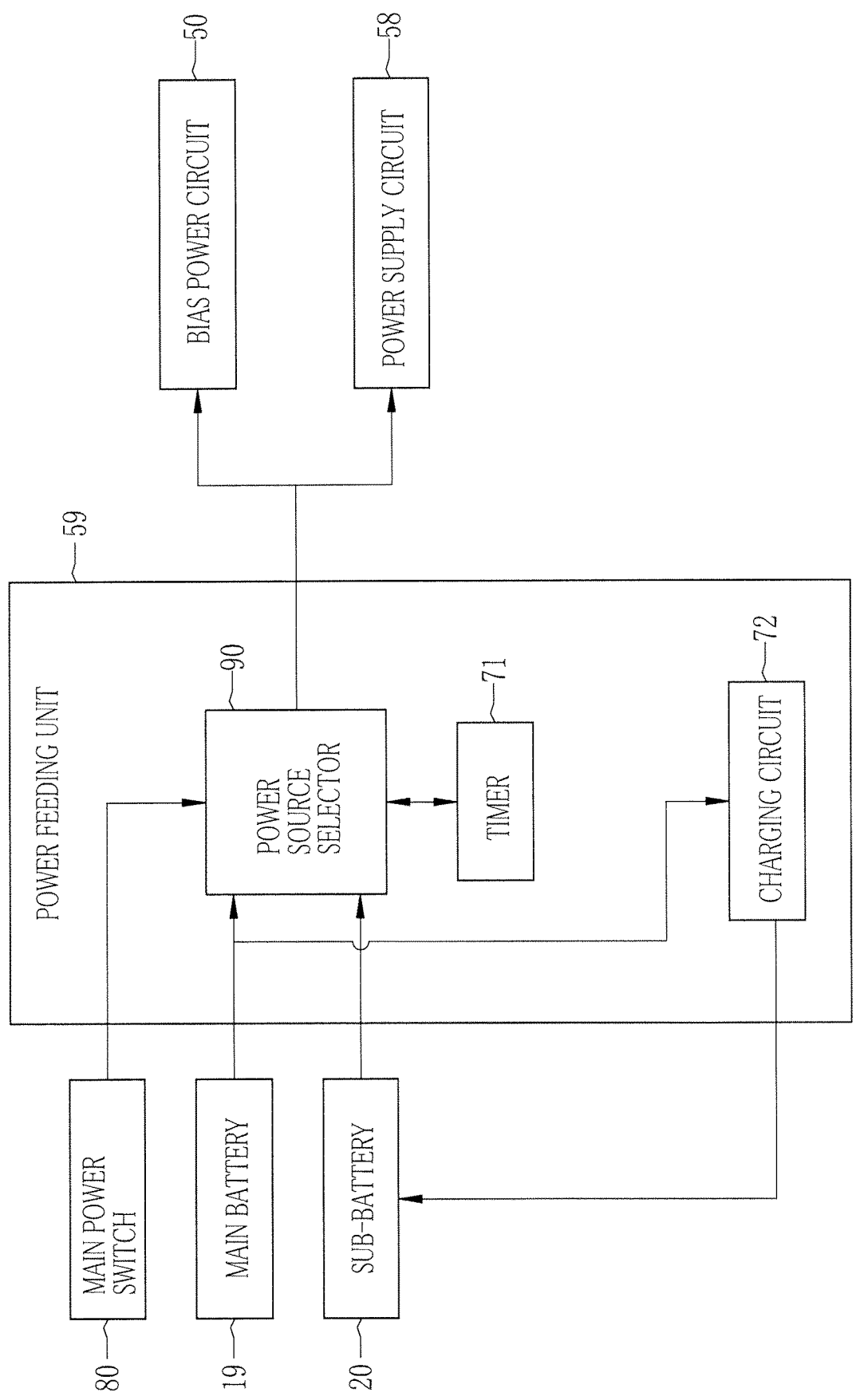
FIG. 16 is a block diagram of a power feeding unit of a third embodiment provided with the main power switch.

In this case, as illustrated in FIG. 16, only an operation signal of the main power switch 80 is input into the power source selector 90. The detachment detection unit 61 is not provided. In addition, the timer 71 is used like the first embodiment mentioned above. The power source selector 90 judges that the replacement operation of the main battery 19 is started when the main power switch 80 is turned off, and changes the power source to the sub-battery 20. Since there is no need to provide the detection unit 61, production cost can be reduced.

Regarding an operation of this embodiment, description is omitted because it is the basically same with the first embodiment, though a trigger of starting the replacement operation of the main battery 19 is changed to the turning off of the main power switch 80 from the detection of the start of the detachment operation of the main battery 19, and a trigger of turning the main power on is changed to the turning on of the main power switch 80 from the attachment of the main battery 19.

In case the main power switch 80 is provided in the housing 21 like in the second and third embodiments mentioned above, since it is necessary to form an opening in the housing 21 where the main power switch 80 is attached into, waterproofness of the housing 21 decreases. Accordingly, it is more preferable that attachment and detachment of the main battery 19 to and from the battery loading unit 36 link on/off of the main power of the electronic cassette 10 as in the first embodiment, than the case that the main power switch 80 is provided in the housing 21 like in the second and third embodiments.

Note that the main power switch may be an operating member provided in the housing 21 like the main power switch 80 of the second and third embodiment, or may be a software operating by on/off command from the control unit without providing an exclusive operating member.

In the embodiments mentioned above, the sub-battery 20 supplies electricity also to the power supply circuit 58 which supplies a drive voltage to neighboring electric circuits such as the scanning circuit 55, the signal processor 56, the memory 57 and the controller 60. However, only the bias power circuit 50 needs electricity from the sub-battery 20 to omit the photoelectric conversion stabilizing process and the offset correction image detecting process, the sub-battery 20 may supply electricity only to the bias power circuit 50.

In case the sub-battery 20 supplies electricity to the power supply circuit 58, though the start-up time TR2 can be more shorten, the sub-battery 20 needs high capacity which requires upsizing of the sub-battery 20. By supplying electricity only to the bias power circuit 50, the sub-battery 20 can be smaller with a smaller capacity.

Fourth Embodiment

In case the electronic cassette 10 is carried from a photography room where a decubitus radiographing table or an upright radiographing table is installed to a sickroom or so on where there is an object for being used alone, the electronic cassette 10 may hit on the floor or the wall by mistake. Therefore, as the electronic cassette 10, there is one having a function to detect an impact to the housing 21 with a sensor. When the detected impact is abnormal, histories such as the detected time and the sensor output at that time may be stored in a storage section, and a warning that the electronic cassette 10 may have broken down may be displayed.

A fall or a collision of the electronic cassette 10 may occur not only during the transportation of electronic cassette 10 but also during the replacement operation of the main battery 19. However, the main power is turned off during the replacement operation of the main battery 19. In case that electricity is not supplied to the sensor to detect an impact, the storage section to store impact histories and so on, an impact that occurred during the replacement operation of the main battery 19 is not recorded as a history. Therefore, in this embodiment, electricity is supplied from the sub-battery 20 to the power supply circuit which supplies a drive voltage to the function to acquire a history of an impact to the housing 21.

Figure 17:
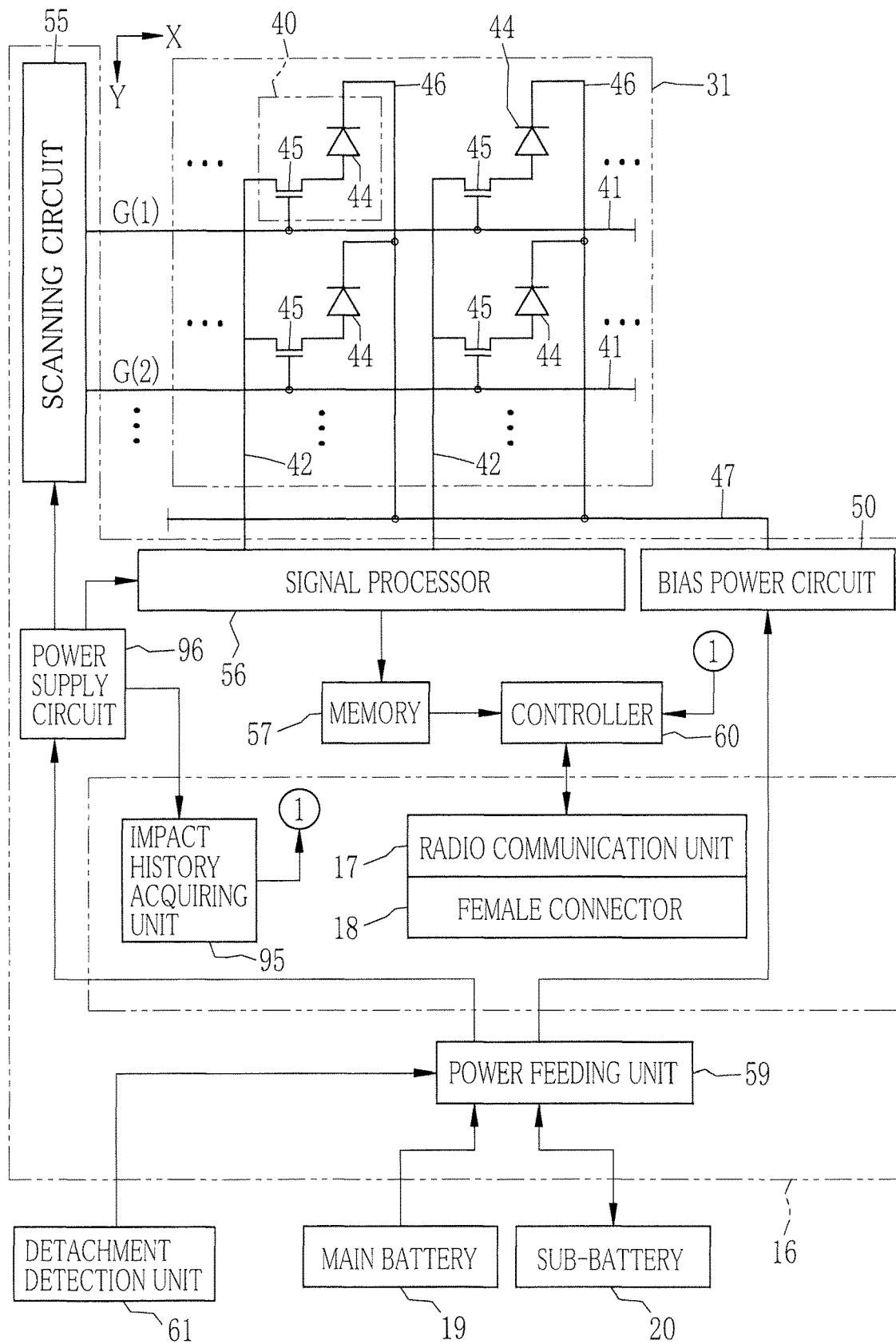
FIG. 17 is a block diagram of an electrical constitution of an electronic cassette of a fourth embodiment provided with an impact history acquiring unit.

As illustrated in FIG. 17, an impact history acquiring unit 95 is provided in the electronic cassette of this embodiment. A power supply circuit 96 supplies a drive voltage to the impact history acquiring unit 95 in addition to the neighboring electric circuits such as the scanning circuit 55, the signal processor 56, the memory 57 and the controller 60, like the power supply circuit 58 of the first embodiment mentioned above. In other words, the power supply circuit 96 corresponds to the third power supply circuit.

Figure 18:
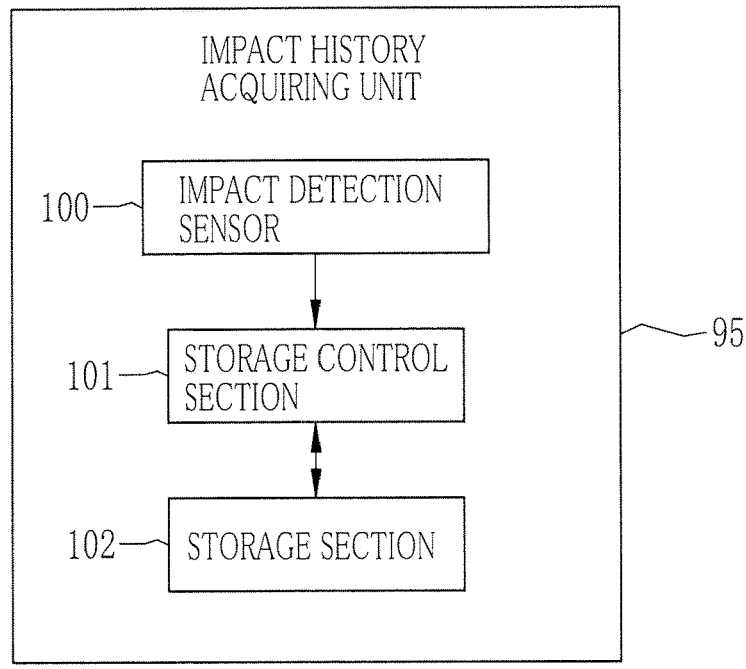
FIG. 18 is a block diagram of the impact history acquiring unit.

As illustrated in FIG. 18, the impact history acquiring unit 95 has an impact detection sensor 100, a storage control section 101 and a storage section 102. The impact detection sensor 100 detects an impact to the housing 21. For example, the impact detection sensor 100 is a three-axes acceleration sensor, which detects an acceleration in each of three-axes directions that are a depth wise direction of the housing 21 at the right angle to the front face 22 and the base face 23, a direction parallel to the side faces 24 and 25, and a direction parallel to the side faces 26 and 27. By an output from the impact detection sensor 100, a direction and a degree of an impact can be found.

The storage control section 101 controls recording of an output from the impact detection sensor 100 the to the storage section 102. When an output from the impact detection sensor 100 is more than a predetermined threshold, the storage control section 101 makes the storage section 102 store histories such as the detected time and the output from the impact detection sensor 100 at that time.

The storage control section 101 outputs a history stored in the storage section 102 in to the controller 60. The controller 60 displays a warning that the electronic cassette 10 may have broken down through an indicator. Note that, the history may be sent to the control unit through the radio communication unit 17 or the female connector 18, so that the warning that the electronic cassette 10 may have broken down will be displayed on a display of the control unit.

Figure 19:
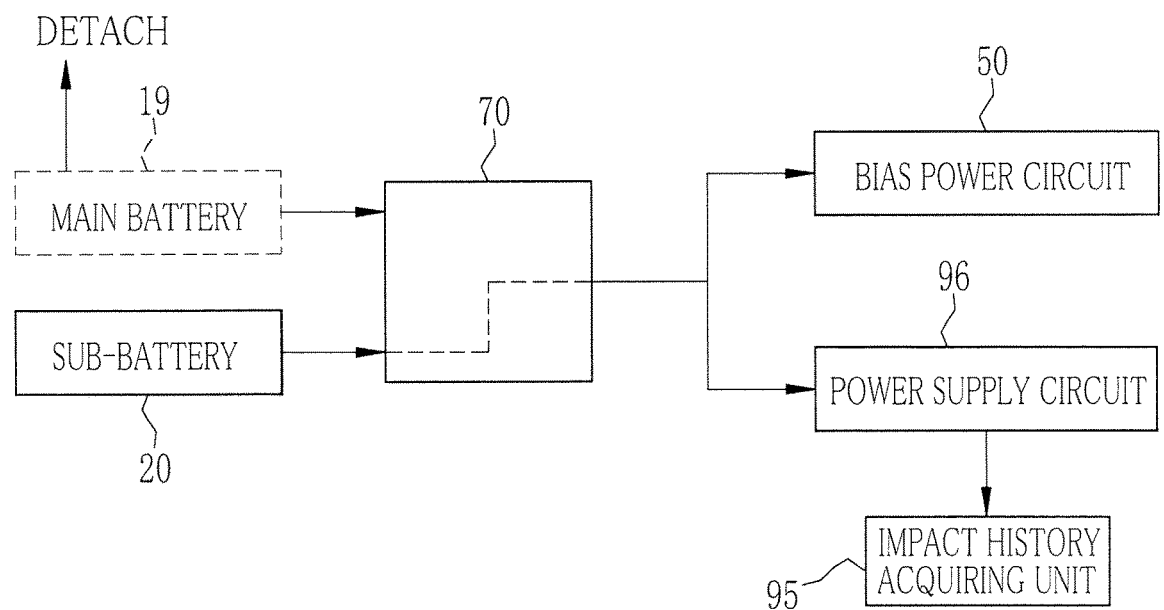
FIG. 19 is a schematic diagram indicating a case of supplying electricity from the sub-battery in the fourth embodiment.

As illustrated in FIG. 19, when the power source selector 70 judges that the replacement operation of the main battery is started, the power source selector 70 changes the power source from the main battery 19 to the sub-battery 20 and make the sub-battery 20 supply electricity to the bias power circuit 50, the power supply circuit 96 and so on. Accordingly, the impact history acquiring unit 95 operates even during the replacement operation of the main battery 19. Therefore, an impact that occurred during the replacement operation of the main battery 19 can be recorded as a history.

A single power supply circuit which is common to the scanning circuit 55, the signal processor 56, other neighboring electric circuits, the impact history acquiring unit 95 and so on may be used like the power supply circuit 58 of the first embodiment and the power supply circuit 96 of the fourth embodiment. Alternatively, it may be provided power supply circuits separately for the parts such as the scanning circuit and the signal processor.

In the above embodiments, the main power is turned off when the main battery 19 is detached from the battery loading unit 36 or when the main power switch 80 is operated. However, the main power may be constituted to be turned off automatically when there is no operation during a predetermined time in the state that the main power is turned on.

Note that, the constitution of the image detection unit 15 is not limited to the constitution that the scintillator 30 is arranged at the X-ray incidence side of the photo detection substrate 31 like the first embodiment, and it may be a constitution that the scintillator 30 is arranged at the side opposed to the X-ray incidence side of the photo detection substrate 31. In this case, the scintillator 30 absorbs X-ray that penetrated the photo detection substrate 31 and generates visible light, and the photo detection substrate 31 detects the visible light. In addition, though the TFT-type image detection unit is illustrated in the above embodiments, a CMOS (Complementary Metal Oxide Semiconductor)-type image detection unit may be used. Furthermore, the present invention can be applied to not only the electronic cassette to photograph based on X-rays, but also an electronic cassette to photograph based on other radiations such as gamma rays.

Various changes and modifications are possible in the present invention and may be understood to be within the present invention.

What is claimed is:

1. An electronic cassette comprising:
   an image detection unit having a plurality of pixels to detect a radiation image of an object based on radiation that penetrated the object;
   a housing of portable type which contains the image detection unit;
   a scintillator that converts the radiation into visible light;
   a plurality of photoelectric converters which constitute the plurality of pixels, generate electric charge in response to the visible light, and accumulate the electric charge;
   a bias power circuit which applies bias voltage to the plurality of photoelectric converters;
   a main battery which is detachably attached to the housing and supplies electricity to the bias power circuit;
   a sub-battery which supplies electricity to the bias power circuit in substitution for the main battery; and
   a power source selector circuit which changes a power source for the bias power circuit from the main battery to the sub-battery after a detachment operation of the main battery is started, the detachment operation being started before the main battery is removed and a supply of the electricity from the main battery is completely cut off.

2. The electronic cassette according to claim 1, further comprising a detachment detection circuit which detects whether the detachment operation is started,
   wherein the power source selector circuit changes the power source of the bias power circuit to the sub-battery in a case where the detachment detection circuit detects a start of the detachment operation.

3. The electronic cassette according to claim 2, further comprising:
   a main power switch for operating on/off of a main power of the electronic cassette according to an operation thereof; and
   a first timer circuit which times a first elapsed time after the main power switch is turned off,
   wherein the power source selector circuit continues to supply the electricity from the main battery till the first elapsed time reaches a predetermined first set time after the main power switch is turned off, and stops the supply of the electricity from the main battery after the first elapsed time reaches the predetermined first set time even when the detachment detection circuit does not detect the start of the detachment operation.

4. The electronic cassette according to claim 1, further comprising a main power switch for operating on/off of a main power of the electronic cassette according to an operation thereof,
   wherein the power source selector circuit judges that the detachment operation is started when the main power switch is turned off.

5. The electronic cassette according to claim 1, further comprising a second timer circuit which times a second elapsed time after the power source selector circuit changes the power source to the sub-battery,
   wherein the power source selector circuit continues to supply the electricity from the sub-battery till the second elapsed time reaches a predetermined second set time, and stops a supply of the electricity from the sub-battery after the second elapsed time reaches the predetermined second set time.

6. The electronic cassette according to claim 1, wherein the power source selector circuit changes the power source for the bias power circuit to the main battery when a main power is turned on while the sub-battery supplies electricity.

7. The electronic cassette according to claim 1, wherein each pixel of the plurality of pixels comprises one of the plurality of photoelectric converters and a switching element connected to a photoelectric converter of the plurality of photoelectric converters to read electric charge,
   wherein the electronic cassette further comprises a driving circuit which drives the switching element and a power supply circuit which supplies a drive voltage for the switching element to the driving circuit, and
   wherein the sub-battery supplies electricity to the power supply circuit.

8. The electronic cassette according to claim 7, further comprising:
   a signal processor which converts electric charge into an image signal constituting the radiation image;
   wherein the power supply circuit supplies a drive voltage to the signal processor, and
   wherein the sub-battery supplies electricity to the second power supply circuit.

9. The electronic cassette according to claim 7, further comprising:
   an impact history acquiring circuit including an impact detection sensor which detects an impact to the housing, a storage section which stores an output from the impact detection sensor, and a storage control circuit which controls a recording of the output from the impact detection sensor to the storage section.

10. The electronic cassette according to claim 9, wherein the sub-battery supplies electricity to the storage section and the storage control circuit.

11. The electronic cassette according to claim 9,
   wherein the power supply circuit supplies a drive voltage to the impact detection sensor, the storage section, and the storage control circuit of the impact history acquiring circuit, and
   wherein the sub-battery supplies electricity to the power supply circuit.

12. The electronic cassette according to claim 9, wherein the storage control circuit makes the storage section store histories based on at least one of an output from the impact detection sensor and times in a case where the output from the impact detection sensor is more than a predetermined threshold.

13. The electronic cassette according to claim 12, further comprising a communication circuit configured to send the histories stored in the storage section to an external device.

14. The electronic cassette according to claim 1, further comprising a charging circuit which charges the sub-battery with electricity from the main battery.

15. An operating method of an electronic cassette, the electronic cassette comprising:
   an image detection unit having a plurality of pixels to detect a radiation image of an object based on radiation that penetrated the object;
   a housing of portable type which contains the image detection unit;
   a scintillator that converts the radiation into visible light;
   a plurality of photoelectric converters which constitute the plurality of pixel, generate electric charge in response to the visible light, and accumulate the electric charge;
   a bias power circuit which applies bias voltage to the plurality of photoelectric converters;
   a main battery which is detachably attached to the housing and supplies electricity to the bias power circuit; and
   a sub-battery which supplies electricity to the bias power circuit in substitution for the main battery,
   the operating method of the electronic cassette comprising steps of:
   changing a power source for the bias power circuit from the main battery to the sub- battery after a detachment operation of the main battery is started, the detachment operation being started before the main battery is removed and a supply of the electricity from the main battery is completely cut off.

* * * * *